(12) United States Patent
Shagam et al.

(10) Patent No.: US 10,241,347 B2
(45) Date of Patent: Mar. 26, 2019

(54) SELF-ALIGNED SPATIAL FILTER

(71) Applicant: Integrated Plasmonics Corporation, San Francisco, CA (US)

(72) Inventors: Michael Yagoda Shagam, San Francisco, CA (US); Robert Joseph Walters, San Francisco, CA (US)

(73) Assignee: INTEGRATED PLASMONICS CORPORATION, San Francisco, CA (US)

( * ) Notice: Subject to any disclaimer, the term of this patent is extended or adjusted under 35 U.S.C. 154(b) by 0 days.

(21) Appl. No.: 15/694,682

(22) Filed: Sep. 1, 2017

(65) Prior Publication Data

US 2018/0011335 A1 Jan. 11, 2018

Related U.S. Application Data

(62) Division of application No. 14/774,990, filed as application No. PCT/US2013/072929 on Dec. 3, 2013, now Pat. No. 9,784,986.

(Continued)

(51) Int. Cl.
*G01N 21/00* (2006.01)
*G02B 27/46* (2006.01)
(Continued)

(52) U.S. Cl.
CPC ............ *G02B 27/46* (2013.01); *B23K 26/384* (2015.10); *B23K 26/402* (2013.01); *C23C 14/34* (2013.01);
(Continued)

(58) Field of Classification Search
CPC ...... G02B 27/46; G02B 27/64; B23K 26/384; B23K 26/402; B23K 2203/18;
(Continued)

(56) References Cited

U.S. PATENT DOCUMENTS 4,516,857 A   5/1985 Preston et al.
4,659,222 A   4/1987 Ekholm
(Continued)

FOREIGN PATENT DOCUMENTS

EP     1 217 426 A1   6/2002
WO   1998/034098 A1   8/1998
(Continued)

OTHER PUBLICATIONS

"Micro-hole drilling with femtosecond fiber laser", by Huang et al., SPIE Paper No. 8607-19, Photonics West 2013, Feb. 2-7, 2013.*
International Search Report (ISR) issued in PCT/US2013/072927 dated Apr. 2014. (Cited in the parent U.S. Appl. No. 14/774,990.).
Written Opinion (PCT/ISA/237) issued in PCT/US2013/072927 dated Apr. 2014. (Cited in the parent U.S. Appl. No. 14/774,990.).
(Continued)

*Primary Examiner* — Jamil Ahmed
(74) *Attorney, Agent, or Firm* — Chen Yoshimura LLP

(57) ABSTRACT

A spatial filter is made by forming a structure comprising a focusing element and an opaque surface, the opaque surface being disposed remotely from the focusing element in substantially the same plane as a focal plane of the focusing element; and by forming a pinhole in the opaque surface at or adjacent to a focal point of the focusing element by transmitting a substantially collimated laser beam through the focusing element so that a point optimally corresponding to the focal point is identified on the opaque surface and imperfection of the focusing element, if any, is reflected on the shape and position of the pinhole so formed.

8 Claims, 30 Drawing Sheets

Related U.S. Application Data

(60) Provisional application No. 61/784,250, filed on Mar. 14, 2013.

(51) Int. Cl.

| | | |
|---|---|---|
| *G01N 21/25* | (2006.01) | |
| *G01N 21/31* | (2006.01) | |
| *B23K 26/384* | (2014.01) | |
| *B23K 26/402* | (2014.01) | |
| *C23C 14/34* | (2006.01) | |
| *C25D 5/02* | (2006.01) | |
| *B23K 103/18* | (2006.01) | |
| *B23K 103/00* | (2006.01) | |

(52) U.S. Cl.
CPC .............. *C25D 5/02* (2013.01); *G01N 21/255* (2013.01); *G01N 21/31* (2013.01); *B23K 2103/18* (2018.08); *B23K 2103/50* (2018.08); *G01N 2201/068* (2013.01); *G01N 2201/0633* (2013.01)

(58) Field of Classification Search
CPC .......... C23C 14/34; C25D 5/02; G01N 21/25; G01N 21/255; G01N 21/31; G01N 2201/0633; G01N 2201/068; G02F 1/13; G02F 1/1335
See application file for complete search history.

(56) References Cited

U.S. PATENT DOCUMENTS

| | | | |
|---|---|---|---|
| 5,116,759 | A | 5/1992 | Klainer et al. |
| 5,644,512 | A | 7/1997 | Chernoff et al. |
| 5,674,457 | A | 10/1997 | Williamsson et al. |
| D433,150 | S | 10/2000 | Wahlqvist et al. |
| 6,838,650 | B1 * | 1/2005 | Toh .................... G02B 21/0024 250/201.3 |
| 7,466,409 | B2 | 12/2008 | Scherer et al. |
| 8,076,128 | B2 | 12/2011 | Liederman et al. |
| 8,231,268 | B2 | 7/2012 | Krol et al. |
| 8,284,401 | B2 | 10/2012 | Choi et al. |
| 2002/0149709 | A1 * | 10/2002 | Uchiyama ............ G03B 21/625 349/2 |
| 2002/0191178 | A1 | 12/2002 | Watkins |
| 2003/0213787 | A1 | 11/2003 | Dunsky et al. |
| 2004/0090621 | A1 | 5/2004 | Bennett et al. |
| 2005/0114332 | A1 | 5/2005 | Lee et al. |
| 2005/0226492 | A1 | 10/2005 | Ho |
| 2006/0034729 | A1 | 2/2006 | Poponin |
| 2007/0070347 | A1 | 3/2007 | Scherer et al. |
| 2008/0135739 | A1 | 6/2008 | Kim et al. |
| 2010/0039648 | A1 | 2/2010 | Garcia Da Fonseca |
| 2010/0046060 | A1 | 2/2010 | Lee et al. |
| 2010/0157306 | A1 | 6/2010 | Choi et al. |
| 2011/0085167 | A1 | 4/2011 | Guan et al. |
| 2011/0111487 | A1 | 5/2011 | Goh et al. |
| 2012/0225475 | A1 | 9/2012 | Wagner et al. |
| 2014/0176939 | A1 | 6/2014 | Shah |
| 2015/0308893 | A1 | 10/2015 | Walters |
| 2015/0377780 | A1 | 12/2015 | Walters et al. |
| 2016/0018329 | A1 | 1/2016 | Walters |
| 2016/0033328 | A1 | 1/2016 | Walters |

FOREIGN PATENT DOCUMENTS

| | | |
|---|---|---|
| WO | 2006/009724 A2 | 1/2006 |
| WO | 2011/106057 A2 | 9/2011 |
| WO | 2012/054351 A2 | 4/2012 |
| WO | 2014/089120 A1 | 6/2014 |
| WO | 2014/123613 A1 | 8/2014 |
| WO | 2014/143235 A1 | 9/2014 |
| WO | 2014/158248 A1 | 10/2014 |

OTHER PUBLICATIONS

Huang et al., "Micro-hole drilling with femtosecond fiber laser", SPIE Paper No. 8607-19, Photonics West 2013, Feb. 2-7, 2013. (Cited in the parent U.S. Appl. No. 14/774,990 and the ISR listed in the Non-Patent Literature document No. 4 below.).
International Search Report (ISR) issued in PCT/US2013/072929 dated Apr. 2014. (Cited in the parent U.S. Appl. No. 14/774,990.).
Written Opinion (PCT/ISA/237) issued in PCT/US2013/072929 dated Apr. 2014. (Cited in the parent U.S. Appl. No. 14/774,990.).
International Search Report (ISR) issued in PCT/US2013/072930 dated Apr. 2014. (Cited in the parent U.S. Appl. No. 14/774,990.).
Written Opinion (PCT/ISA/237) issued in PCT/US2013/072930 dated Apr. 2014. (Cited in the parent U.S. Appl. No. 14/774,990.).
International Search Report (ISR) issued in PCT/US2013/072932 dated Apr. 2014. (Cited in the parent U.S. Appl. No. 14/774,990.).
Written Opinion (PCT/ISA/237) issued in PCT/US2013/072932 dated Apr. 2014. (Cited in the parent U.S. Appl. No. 14/774,990.).
International Search Report (ISR) issued in PCT/US2013/072936 dated Apr. 2014. (Cited in the parent U.S. Appl. No. 14/774,990.).
VVritten Opinion (PCT/ISA/237) issued in PCT/US2013/072936 dated Apr. 2014. (Cited in the parent U.S. Appl. No. 14/774,990.).
Fiedler, "Incoherent Broad-Band Cavity-Enhanced Absorption Spectrscopy", 2005, Berlin. (Cited in the parent U.S. Appl. No. 14/774,990 and in the ISR listed in the Non-Patent Literature document No. 10 above.).
Barron, "Basics of UV-Visible Spectroscopy", Physical Methods in Chemistry and Nano Science, Jun. 5, 2010. (Cited in the parent U.S. Appl. No. 14/774,990 and in the ISR listed in the Non-Patent Literature document No. 10 above).
Chen et al., "A CMOS Image Sensor Integrated with Plasmonic Colour Filters", Plasmonics, Dec. 2012, vol. 7, Issue 4, (abstract) Springer-Link. (Cited in the parent U.S. Appl. No. 14/774,990 and in the ISR listed in the Non-Patent Literature document No. 10 above).
Mansuripur et al., "Plasmonic nano-structures for optical data storage", Optics Express, Aug. 3, 2009, vol. 17, No. 16, pp. 14001-14014. (Cited in the parent U.S. Appl. No. 14/774,990 and in the ISR listed in the Non-Patent Literature document No. 10 above).
Genet et al., "Light in tiny holes", nature, Jan. 4, 2007, vol. 445, pp. 39-46. (Cited in the parent U.S. Appl. No. 14/774,990 and in the ISR listed in the Non-Patent Literature document No. 10 above).
Koerkamp et al., "Strong Influence of Hole Shape on Extraordinary Transmission through Periodic Arrays of Subwavelength Holes", Physical Review Letters, May 7, 2004, vol. 92, No. 18, pp. 183901-1 183901-4. (Cited in the parent U.S. Appl. No. 14/774,990.).
Jones et al., "Surface Plasmon assisted extraordinary transmission in metallic nanohole arrays and its suitability as bio-sensor", Journal of Physics: Conference Series 307, IOP Publishing, 2011, pp. 1-7. (Cited in the parent U.S. Appl. No. 14/774,990.).
Tok et al., "Unidirectional broadband radiation of honeycomb plasmonic antenna array with broken symmetry", Optics Express, Nov. 7, 2011, vol. 19, No. 23, pp. 22731-22742. (Cited in the parent U.S. Appl. No. 14/774,990.).
Pacifici et al., "Universal optical transmission features in periodic and quasiperiodic hole arrays", Optics Express, Jun. 9, 2008, vol. 16, No. 12, pp. 9222-9238. (Cited in the parent U.S. Appl. No. 14/774,990.).
Singh et al., "Surface Plasmon Resonance Enhanced Transmission of Light through Gold-Coated Diffraction Gratings", Analytical Chemistry, May 15, 2008, vol. 80, No. 10, pp. 3803-3810. (Cited in the parent U.S. Appl. No. 14/774,990.).
U.S. Appl. No. 14/095,971, filed Dec. 3, 2013.
U.S. Appl. No. 14/648,843, filed Jun. 1, 2015.
U.S. Appl. No. 14/766,551, filed Aug. 7, 2015.
U.S. Appl. No. 14/775,266, filed Sep. 11, 2015.
U.S. Appl. No. 14/775,299, filed Sep. 11, 2015.

\* cited by examiner

601

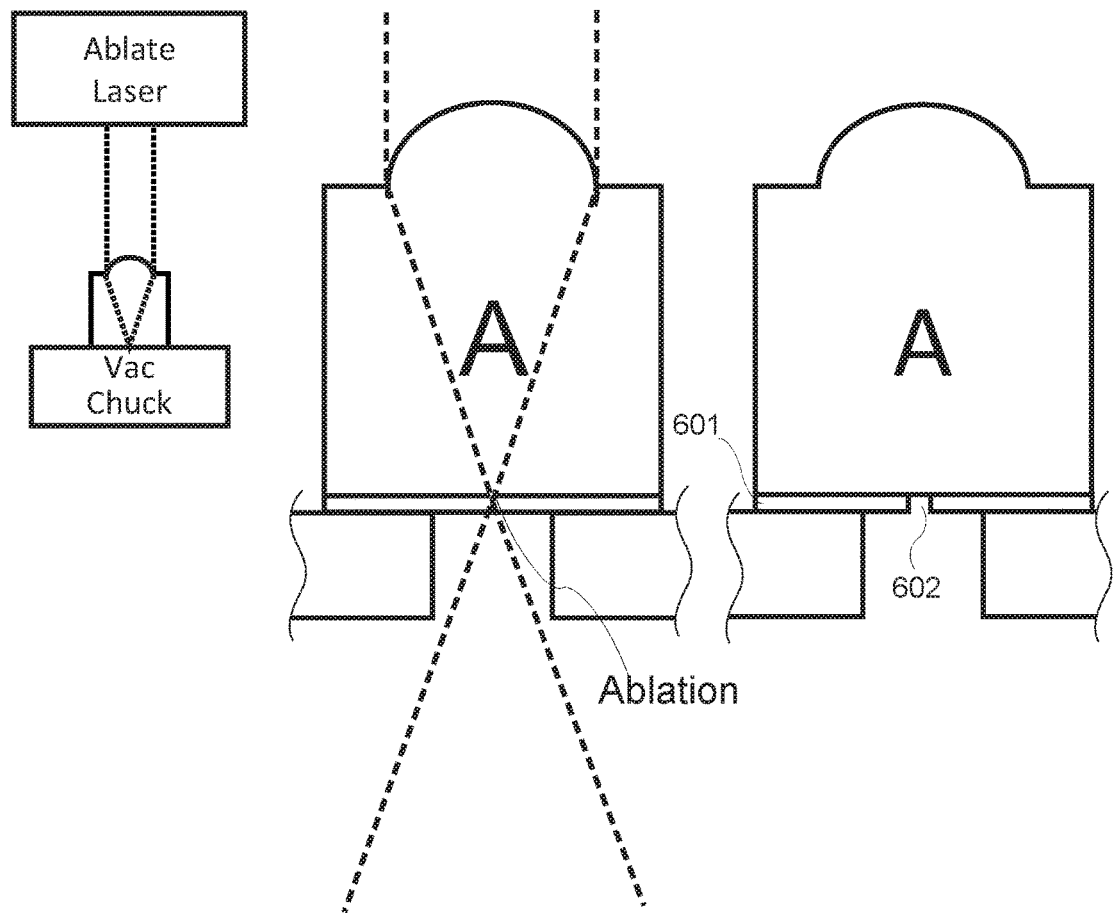

Slip-fit tube

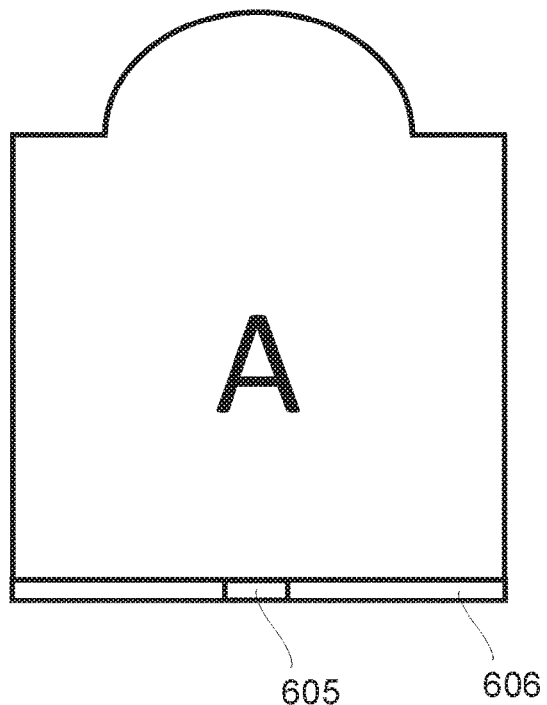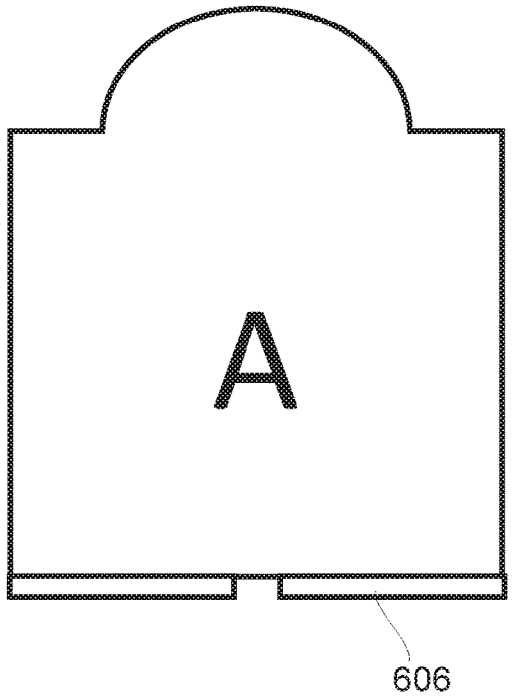

FIG. 6S
FIG. 6T
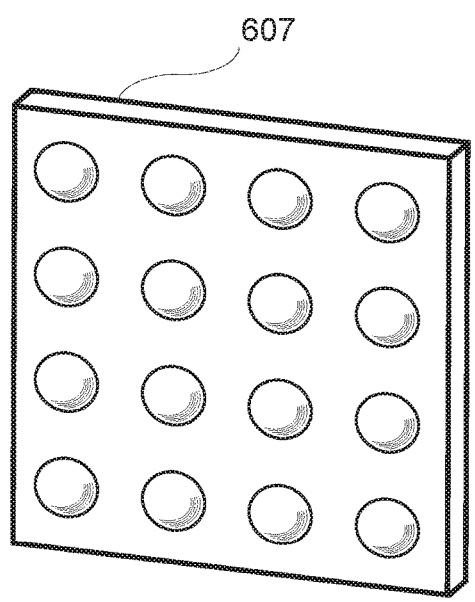
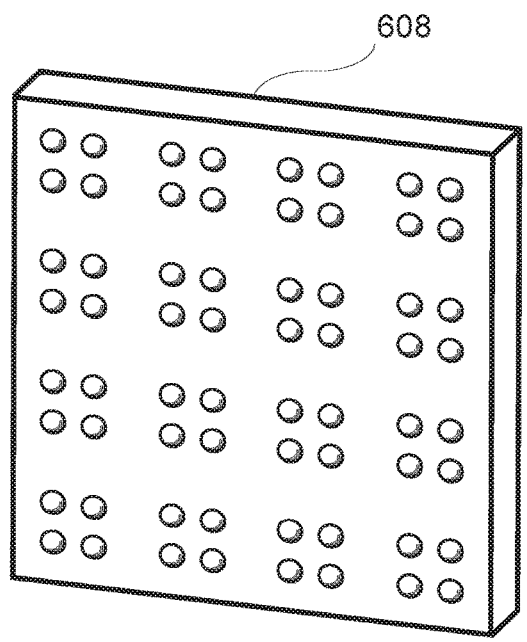

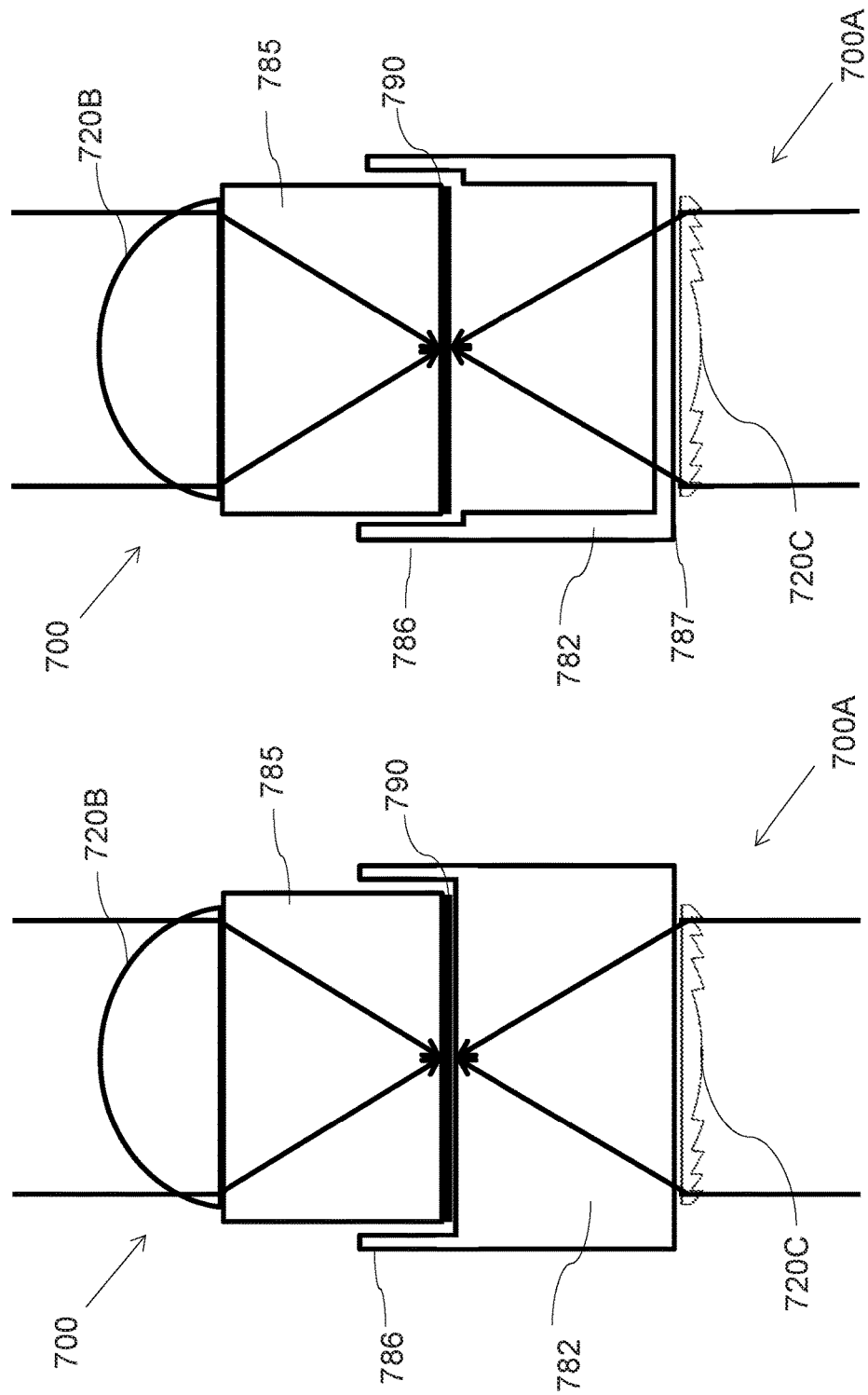

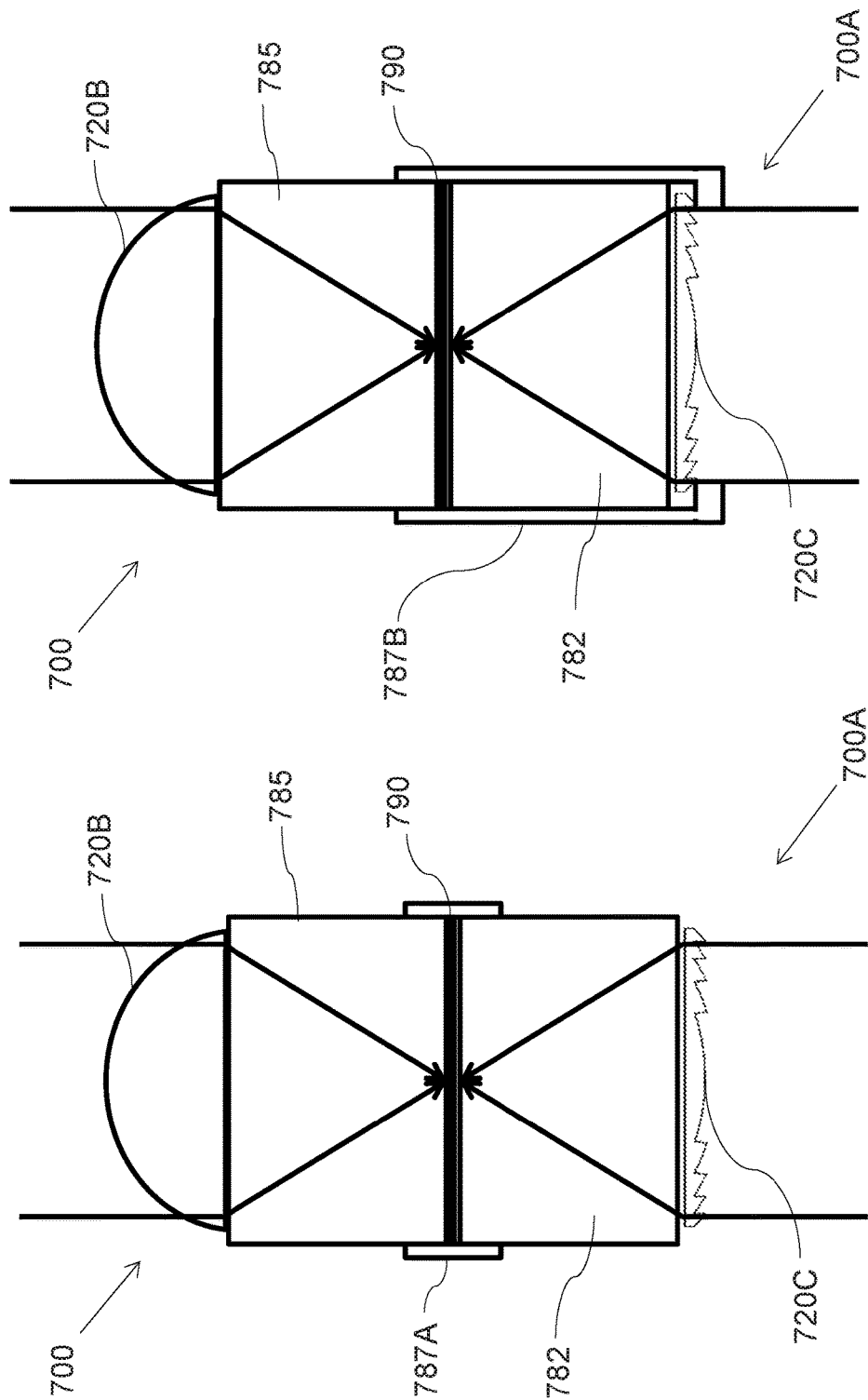

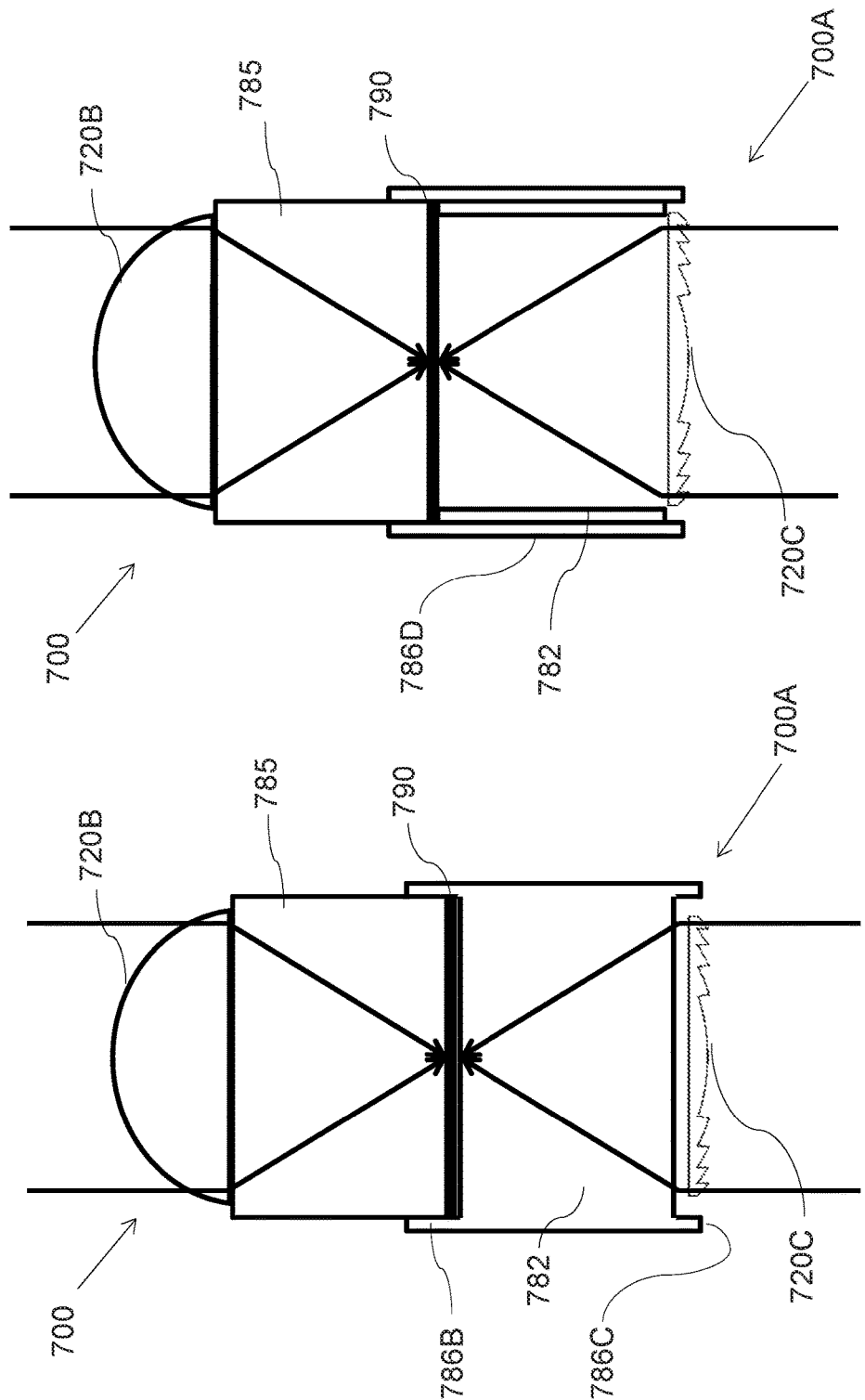

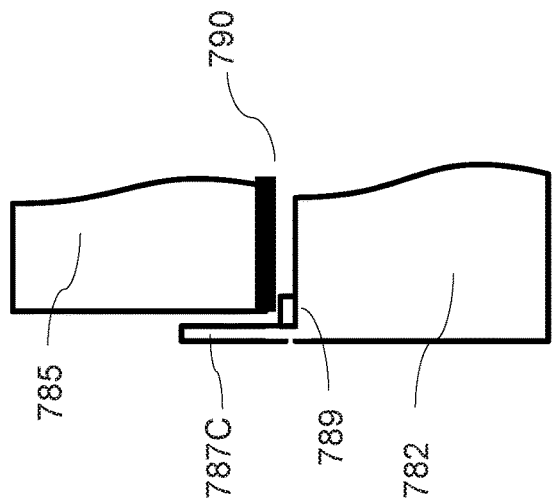
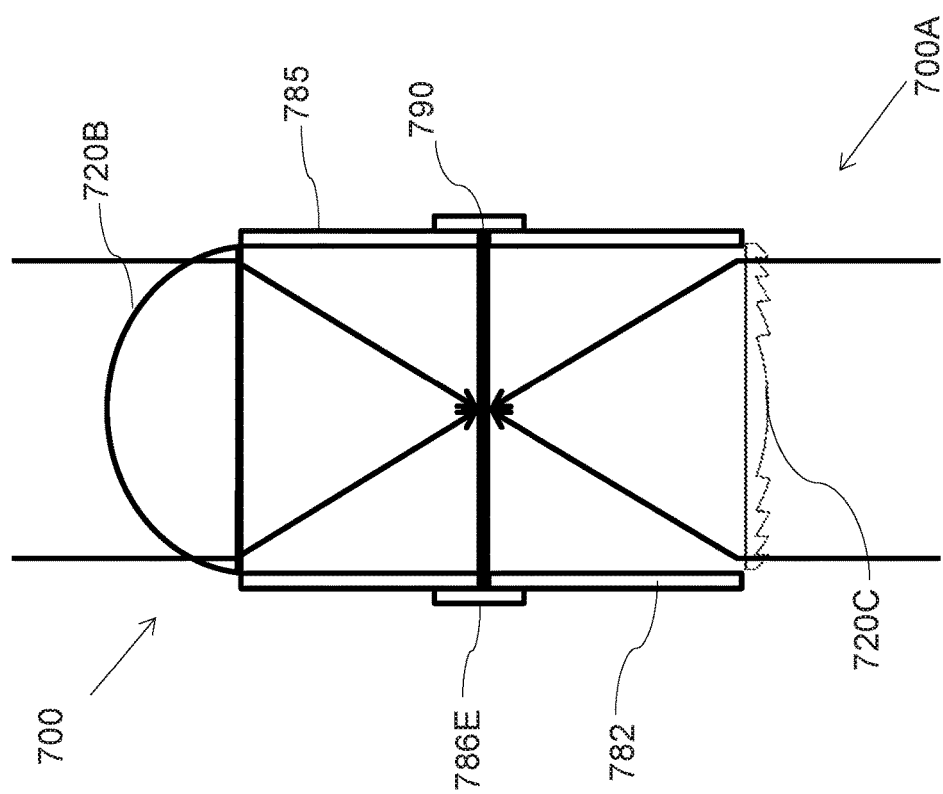
FIG. 7M
FIG. 7L

SELF-ALIGNED SPATIAL FILTER

BACKGROUND

1. Field of the Invention

This invention relates to a spatial filter, and more particularly, to a spatial filter adequate for implementation in compact optical devices, such as personal health-monitoring devices for distributed healthcare and point-of-care consumer health monitoring devices and to manufacture methods therefor.

2. Description of the Related Art

Micro or sub-millimeter scale pinholes are typically used as spatial filters in precision optical scientific instruments such as interferometers, alignment and inspection instrumentation to perform such functions such as cleaning up laser beam spatial profiles or collimating a finite sized light source in a desired direction. They typically require minimally 3 degrees of freedom with micro-scale resolution and a skilled technician or engineer to align. Such existing spatial filters do not lend itself well for an optically based consumer electronics device where fast volume production is generally necessary.

In light of the above and in view of a general trend for portable and personal monitoring of biochemical substances in the users, there exists a need for an optical filter system and method for making it that are suitable for implementation in cost-efficient and robust optical devices, such as portable self-monitoring devices for distributed diagnostics and personal or home healthcare.

SUMMARY OF THE INVENTION

An object of the present invention is to solve one or more of problems or disadvantages of the prior art technologies, certain aspects of which are described above.

To achieve one or more of these and other advantages and in accordance with the purpose of the present invention, as embodied and broadly described, in one aspect, the present invention provides a method for making a spatial filter, including: forming a structure having a focusing element and an opaque surface, the opaque surface being disposed remotely from the focusing element in substantially the same plane as a focal plane of the focusing element; and forming a pinhole in the opaque surface at or adjacent to a focal point of the focusing element by transmitting a substantially collimated light beam through the focusing element so that a point optimally corresponding to the focal point is identified on the opaque surface and imperfection of the focusing element, if any, is reflected on the shape and position of the pinhole so formed.

In another aspect, the present invention provides a self-aligning system for blocking light that is not collimated in a desired direction, the system including: a focusing element; a recollimating element, the focus of which is coincident with the focus of the focusing element; and a planar pinhole element, the plane of which is substantially coincident with the focus of the focusing element and the focus of the recollimating element, the pinhole element having a self-aligned pinhole that is formed through transmitting a substantially collimated light beam through either the focusing element or the recollimating element to the focus so that a point optimally corresponding to the focal point is identified on the opaque surface and imperfection, if any, of the focusing element or the recollimating element is reflected on the shape and position of the self-aligned pinhole so formed.

In another aspect, the present invention provides a spatial filter for blocking light that is not collimated in a desired direction, the spatial filter including: a first focusing element having a focal point; a second focusing element having a focal point, the second focusing element being disposed opposite to the first focusing element such that the respective focal points substantially coincide with each other; a middle plate having an opaque surface interposed between the first focusing element and the second focusing element, the middle plate having a pinhole in the opaque surface at or adjacent to the focal points of the first and second focusing elements; and a non-adjustable supporting structure to support the middle plate and at least one of the first and second focusing elements to define a non-adjustable fixed positional relationship between the middle plate and said at least one of the first and second focusing elements.

In another aspect, the present invention provides a detecting system that includes: a light source; a container for containing a specimen to be analyzed; the container being optically coupled with the light source to receive light from the light source; a spatial filter or self-aligning system as described above, the spatial filter/self-aligning system being configured to receive light that has interacted with the specimen in the container and to transmit substantially collimated components of the light that has interacted with the specimen; and a detector that receives the substantially collimated components of the light that has interacted with the specimen to measure one or more properties of the specimen based on the received light components.

Among other advantages that will be made clear from the descriptions below, certain aspects of this invention make it possible to quickly fabricate spatial filter modules in single lens or multiple lenses (lenslet) geometries in either single or batch volumes, without having to actively align the spatial filter to the focusing optic. These spatial filters may not be of high performance because the process mainly relies on machining tolerances and other factors such as the degree of the collimation in the laser beam used for fabrication, but are adequate for use in various applications, including, but not limited to, inexpensive, non-scientific optical instrumentation, such as point of care consumer health monitoring devices. In addition, when the non-adjustable supporting structure described above is employed, the positional relationship between the optical elements is fixed, and the reliability and stable performance are ensured.

Additional features and advantages of the invention will be set forth in the description which follows and in part will be apparent from the description, or may be learned by practice of the embodiments of the invention disclosed herein. The other objectives and advantages of the invention will be realized and attained by the structure particularly pointed out in the written description and claims hereof and/or in the appended drawings.

It is to be understood that both the foregoing general description and the following detailed description are exemplary and explanatory, and are intended to provide further explanation of the invention as claimed in a patent(s) originating from this application.

BRIEF DESCRIPTION OF THE SEVERAL VIEWS OF THE DRAWINGS

FIGS. 7A to 7M illustrate various embodiments of spatial filters or spatial filter arrays and their alignment methods according to embodiments of the present invention.

DETAILED DESCRIPTIONS OF EMBODIMENTS

Figure 1:
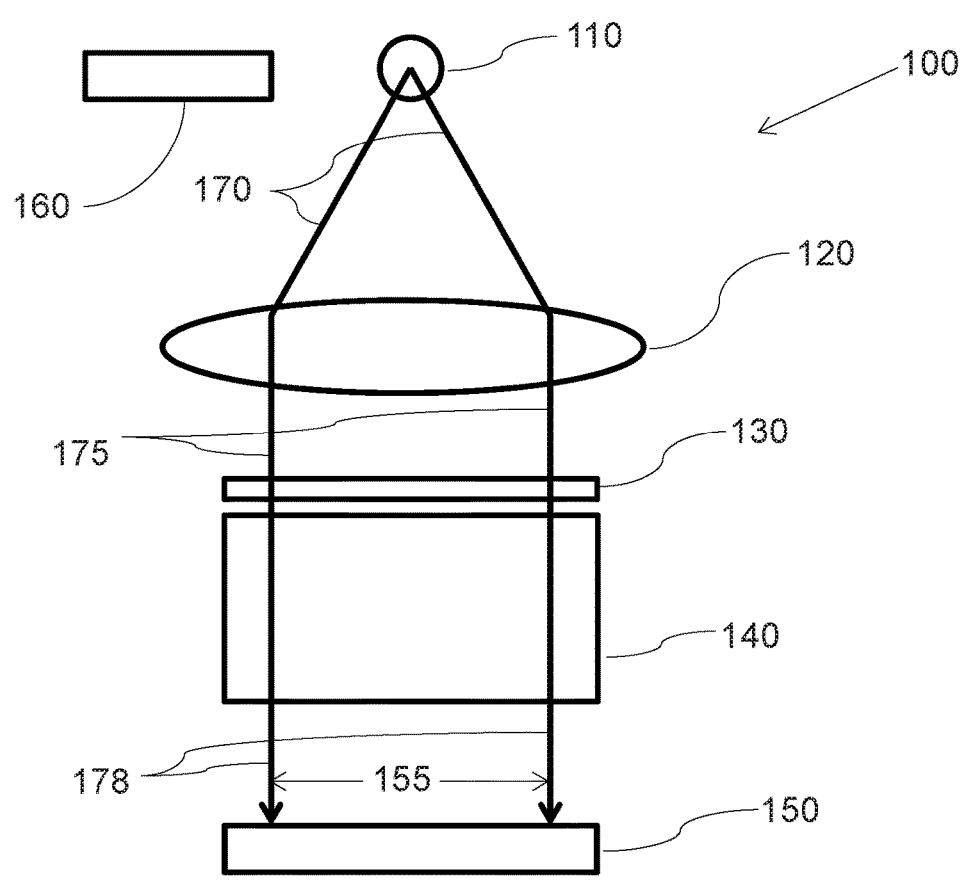
FIG. 1 depicts a schematic of an absorption spectroscopic monitoring device with idealized optical paths shown.

Embodiments are described in detail with reference to the drawings. Features and structures contained in attached drawings are schematic representations of embodiments of the present invention and are not drawn to scale; relative dimensions of the features and structures depicted are not accurate. In particular, for ease of explanation and illustration, even in the same drawings, some of the features or structures are exaggerated or magnified by one or more orders of magnitudes as compared with other features of the drawings.

In typical absorption spectroscopic analysis of an analyte, probing light of a certain bandwidth is configured to interact with the analyte. The analyte absorbs some components of the probing light. The spectrum of the light transmitted through the analyte is compared with the spectrum of the probing light to quantitatively and qualitatively measure properties of the analyte.

In order to analyze the spectrum of the transmitted light in a small, portable device adequate for personal healthcare, for example, plasmonic color filters utilizing surface plasmons have been being proposed recently. See a concurrently filed, commonly owned PCT International Application No. PCT/US2013/072927, entitled "Plasmonic Spectroscopic Sensor And Cuvette Therefor," designating the U.S. and claiming the benefit of Provisional Application No. 61/734,934, filed Dec. 7, 2012. That PCT International Application is hereby incorporated by reference in its entirety. Plasmonic color filters can be made small and can be manufactured in an array in a relatively simple and inexpensive manner. Examples of the plasmonic color filter disclosed in that PCT International Application include, but are not limited to, a periodic array of pinholes formed in a metal layer, an aperiodic array of pinholes formed in a metal layer, a quasi-periodic array of pinholes formed in a metal layer. By appropriately designing the dimensions of the arrays/pinholes and their patterns, various transmission characteristics can be achieved. Thus, as disclosed in the above-referenced PCT International Application, an array of the plasmonic filters having different patterns may be configured to receive light that has interacted with the analyte, and by detecting the intensities of the light transmitted through the array of plasmonic filters, the spectrum of the light that has interacted with the analyte can be reconstructed to the degree required for the purpose of the sensor device.

With certain designs of the plasmonic filters, however, the transmission characteristics of the filters are sensitive to the incident angle of the incoming light. That is, the transmission spectrum of the filter may deviate from its originally intended design when the incident angle is not substantially perpendicular to the detection surface, for example. Similar problems may exist in optical elements utilizing photonic crystal and in other optical devices utilizing diffraction phenomena. This angle-sensitive nature of the optical elements may degrade the detection accuracy of the sensor device.

Furthermore, more generally, when a system is designed to be operative with collimated light, an idealized system has perfectly collimated light both going into and out of the sample volume, something that rarely occurs in most systems. As a result, such systems routinely need well aligned slits or pinholes to block imperfectly collimated light. Alignment of the slits or pinholes can be mechanically complex, requiring many axes of freedom, and potentially requiring significant time to perform the alignment. Some systems have automated mechanisms to perform the alignment of the system, which may require additional sensors and software.

When a system is designed to be operative with collimated light, collimation of input light sources may be particularly needed if the source is not a laser. The collimation of a source such as a light emitting diode (LED) is limited in part by the physical size of the source. Similarly, the collimation of a system which utilizes ambient light or which utilizes sunlight as a source will typically have significant amounts of scattered light which may need to be blocked.

Scattering of light may also occur from different elements within the optical system, and may occur within the sample volume, particularly when higher concentrations of sample are present within the sample volume. In such a case, if the detector or color filter is designed to accurately measure the transmitted light when the light is normally incident to the detection or filter surface, the scattered light may cause significant degradation in the actual measurement results.

The mechanisms required for collimating light into or out of the sample volume are frequently large, expensive, and may require maintenance to realign the system if the system is moved or dropped. Typically, three or more axes of freedom need to be adjusted by a skilled technician or an automation system. The present inventors have come to realize that for certain improvements of portable spectroscopy systems, for example, an easily manufactured, inexpensive, simple, and robust collimator system or spatial filter which blocks non-collimated or improperly collimated light and scattered light is needed.

To further illustrate some of the problems described above, the need for collimating light in case of an absorption spectroscopic device is illustrated with reference to FIGS. 1 and 2.

FIG. 1 schematically shows a configuration of an example of a portable absorption spectroscopic monitoring system 100 similar to certain examples disclosed in the above-referenced PCT International Application. The system 100 has a point light source 110 powered by drive electronics 160, which produces divergent input light 170 having a certain spectral bandwidth. Depending on applications, the wavelength range of the input light may be visible light wavelengths, UV and/or far IR wavelengths. The input light 170 is collimated by one or more optical elements 120, and may be filtered by an optional filter 130 before the collimated light 175 passes through a sample volume 140. A sample volume 140 may be configured as a container for containing a fluid specimen to be analyzed, for example. The collimated light 175 interacts with the specimen of the sample volume 140. In the case of linear absorption spectrum analysis, the interaction between the collimated light 175 and the specimen results in spectrally differentiable absorption of the collimated light 175. That is, some portions of the spectrum of the light entering into the sample volume 140 are absorbed by the specimen in the sample volume. As a result, light 178 that emerges from the sample volume 140 has a spectrum that is different from the spectrum of the light incident on the sample.

A sensing device 150 is provided to receive the transmitted light 178 to analyze the spectrum of the light 178. As described above, if plasmonic color filters or diffraction-controlled optical elements are used in the sensing device 150, the system needs to be configured such that the sensing device 150 receives light from a predetermined incident angle(s) with a relatively narrow tolerance in order to accurately determine the spectrum of the incoming light. In the example depicted in FIG. 1, the sensing device 150 is arranged to receive the light 178 such that the light 178 impinges upon the sensor surface perpendicularly.

If there occurs no scattering or other anomalies in the optical paths of the light 170, 175, 178 that pass through the optical element 120 (and the filter 130, if any) and the sample volume 140, all the components of the output light 178 would be collimated and would enter the sensing device 150 perpendicularly. This idealized optical path is depicted by the lines 170 and 178 in FIG. 1. Such an idealized system does not consider any changes in propagation due to optical scattering, particularly from scattering due to interaction with specimen or other particles in the sample volume 140, or scattering from any of one or more optical elements 120, optical filter 130, or the sample volume 140. The system is further assumed to have perfect collimation after one or more optical elements 120, which cannot occur even with an infinitely small source due to geometric and/or chromatic aberrations in the optical element 120. Other optical defects such as dust, fringing, scratch and dig defects in any optical elements which may also contribute to absorption and scattering are also not considered. In reality, these perturbations and defects may cause significant portions of the output light 178 obliquely enter the sensing device 150, which in turns may cause inaccuracy in the detection results of the sensing device 150. If the target precision and accuracy of the system 100 can tolerate such inaccuracies, the system 100 may be used as configured in FIG. 1. However, the present inventors have come to realize that in order to improve the accuracy and precision of the device, further improvement in the system configuration may be needed.

Figure 2:
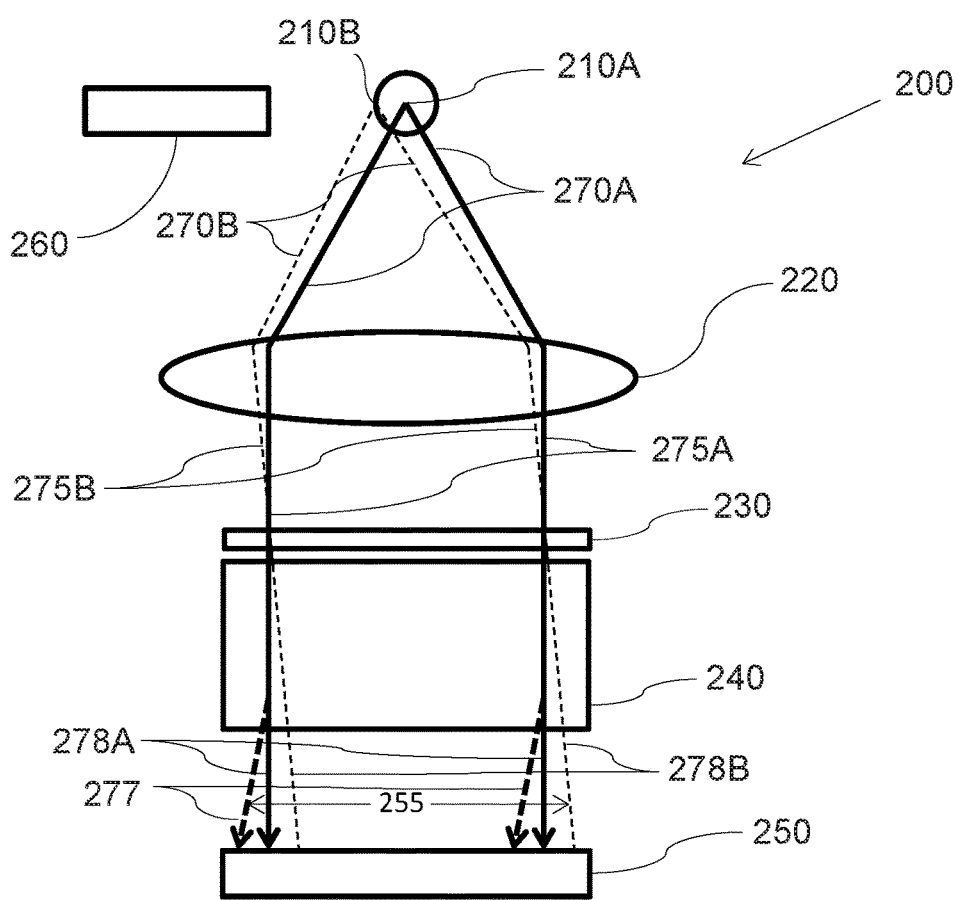
FIG. 2 depicts a schematic of an absorption spectroscopic monitoring device with realistic optical paths shown.

FIG. 2 depicts optical paths of the illumination light when some of the above-described perturbations are taken into account. The system 200 shown in FIG. 2 has a finite-sized light source spanning laterally between an on-axis source object field point 210A and off-axis source object field point 210B powered by drive electronics 260, which produces a continuum of divergent input light spanning between on-axis divergent light 270A and off-axis divergent light 270B. The off-axis divergent light 270B is imperfectly collimated by one or more optical elements 220 in a direction angularly offset from the optical axis of the optical element 220 (i.e., the vertical direction in the figure) as imperfectly collimated input light 275B. The on-axis divergent light 270A is collimated by one or more optical elements 220 in a direction coincident with the optical axis of the optical element as paraxially collimated input light 275A. As in FIG. 1, the light 275A and 275B may be filtered by an optional filter 230 before the sample volume 240. The paraxially collimated input light 275A (that is, light collimated in the vertical direction) and imperfectly collimated input light 275B interact with specimen in the sample volume 240. Scattered light 277 is generated from sample volume 240 due to factors mentioned above. Scattered light 277, imperfectly collimated output light 278B, and paraxially collimated output light 278A are all detected by sensor 250.

Figure 3A:
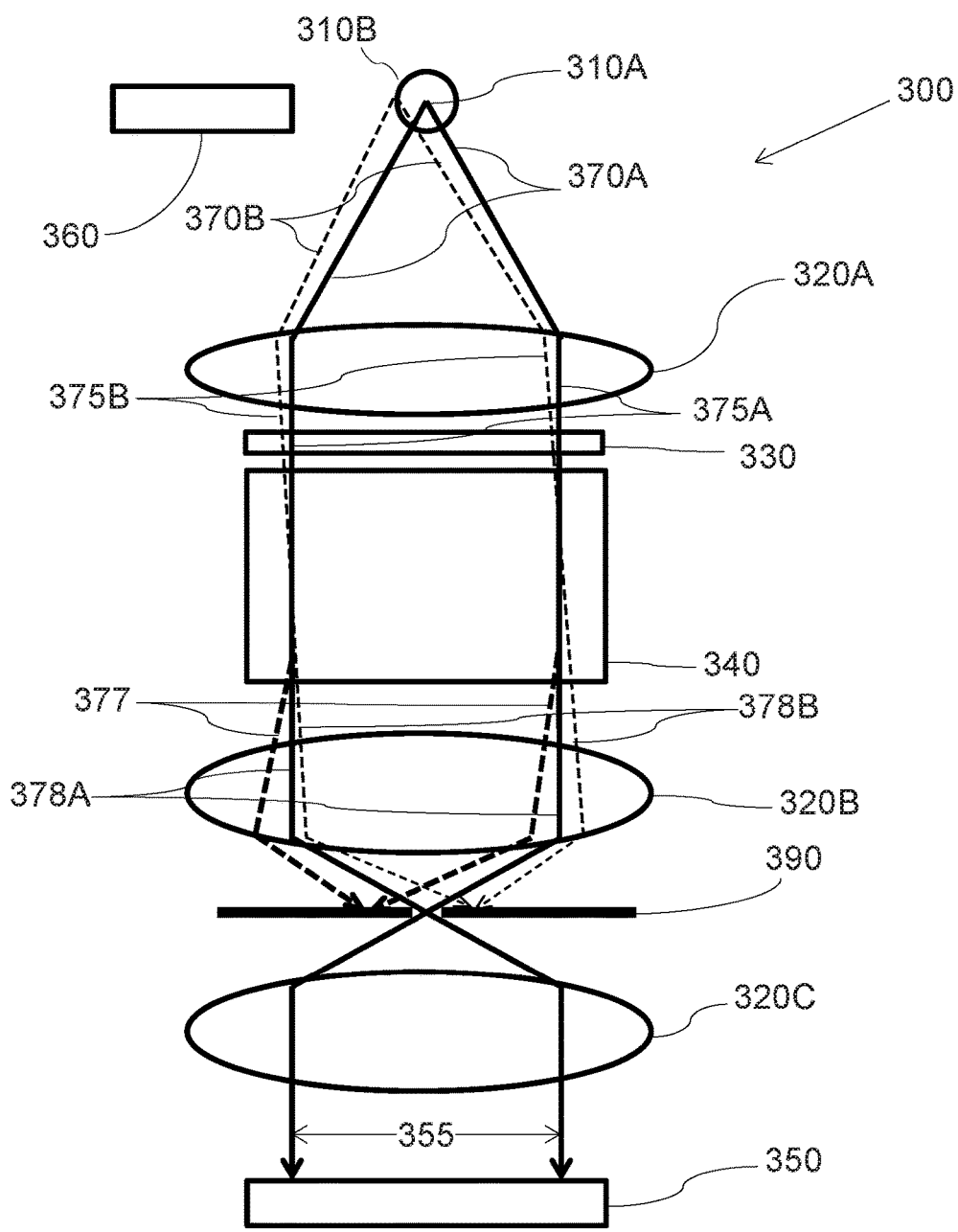
FIG. 3A depicts a schematic of an absorption spectroscopic monitoring device with a spatial filter according to an embodiment of the present invention.

FIG. 3A schematically depicts a system 300 according to an embodiment of the present invention. The reference numerals starting with the number "3" indicate the same or similar components as those depicted with the reference numerals starting with the numbers "1" and "2" bearing the same last two digits in FIGS. 1 and 2, respectively. As shown in FIG. 3A, in this embodiment, the system 300 additionally includes a pinhole element 390 and lens-pair 320B and 320C for substantially rejecting light components that are not collimated vertically.

Similarly to the system depicted in FIG. 2, this system 300 has a finite size light source spanning laterally between an on-axis object source field point 310A and off-axis object source field point 310B powered by drive electronics 360, which produces a continuum of divergent input light spanning between on-axis divergent light 370A and off-axis divergent light 370B. The off-axis divergent light 370B is imperfectly collimated by one or more optical elements 320 in a direction angularly offset from the optical axis of the optical element 320 (i.e., the vertical direction in the figure) as imperfectly collimated input light 375B. The on-axis divergent light 370A is collimated by one or more optical elements 320 in a direction coincident with the optical axis of the optical element as paraxially collimated input light 375A. As in FIG. 1 and FIG. 2, the light 375A and 375B may be filtered by an optional filter 330, and may pass through the sample volume 340, wherein the input light may interact with specimen within the sample volume 340. The interaction between the paraxially collimated input light 375A and imperfectly collimated input light 375B and the specimen may result in spectrally differentiable absorption of the light. Scattered light 377 is generated from sample volume 340. As can be seen in FIG. 3A, paraxially collimated output light 378A (i.e., the light collimated along the vertical direction) is focused by focusing element 320B through pinhole element 390, and directed towards sensing device 350 by recollimating element 320C. However, imperfectly collimated output light 378B (diverging or converging light or light that is off-axis collimated) and scattered light 377 will strike the pinhole element and will be absorbed, scattered, or reflected. The field of view 355 which strikes the sensing device 350 has substantially no component of light 378B and 377. Thus, this configuration can ensure that the light impinging upon the sensing device 350 is perpendicular to the surface of the sensing device 350. This configuration therefore enables the use of plasmonic color filter or other diffraction type optical elements in the sensing device 350 that require the incidence angle to be perpendicular (or in any predetermined design direction) with minimized variation of incidence angle to the detection surface for accurate or improved analysis.

In FIG. 3A, the magnification of elements 320B and 320C is shown as being unity or one (the focal lengths of elements 320B and 320C are the same) but could vary if the design requires magnification greater than one or less than one.

System 300 requires proper alignment of focusing element 320B, pinhole element 390, and re-collimation element 320C with respect to the distance between the elements, the planarity with respect to the elements, and the optical centration of the elements.

Figure 3B:
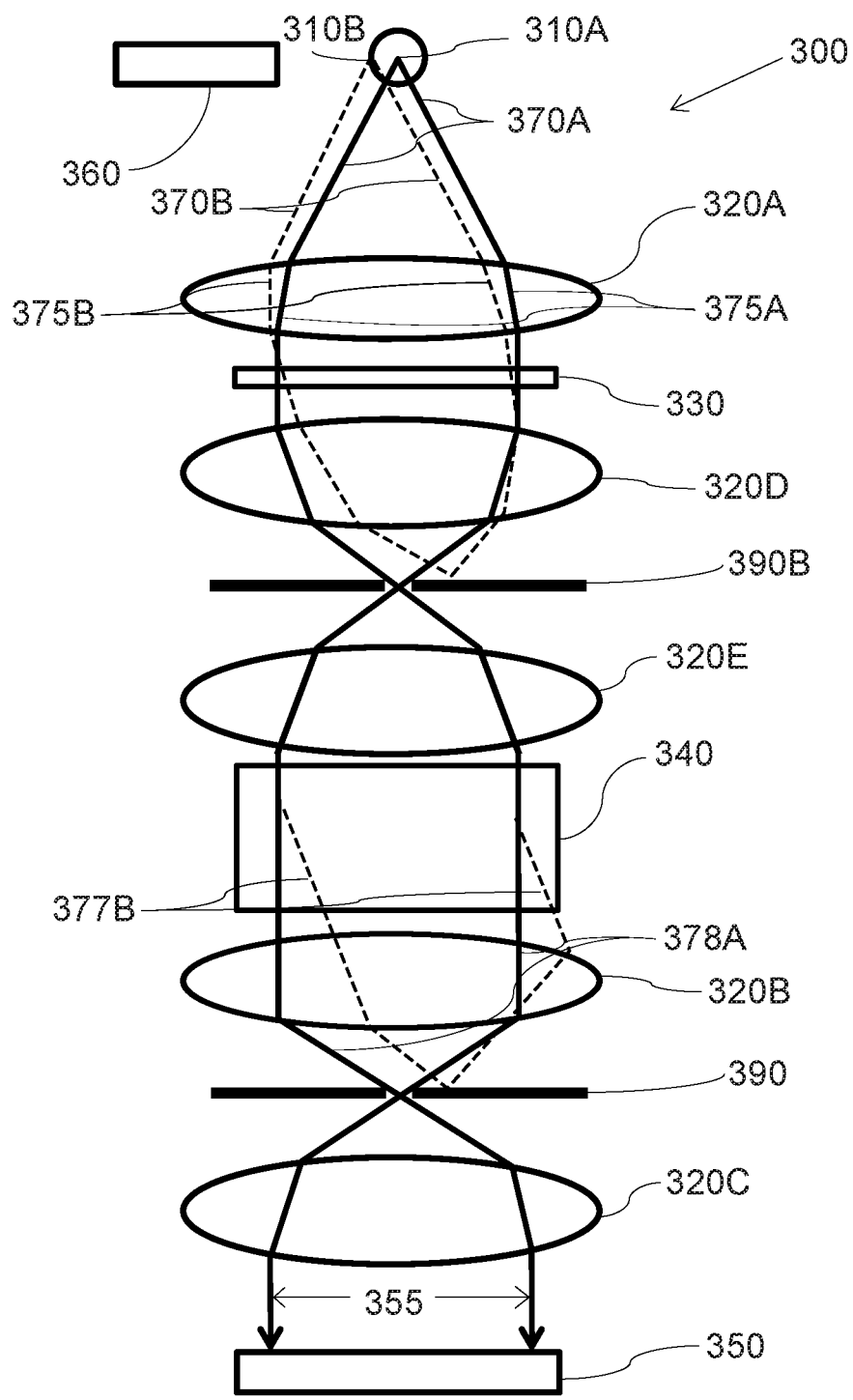
FIG. 3B depicts a schematic of an absorption spectroscopic monitoring device with two spatial filters according to an embodiment of the present invention.

FIG. 3B schematically depicts another embodiment of the present invention. In addition to the components as described above, this system includes an additional focusing element 320D, additional recollimating element 320E and additional pinhole element 390B placed before the sample volume 340 to remove off-axis collimated light and other unintended light components from the light before entering the sample volume 340.

In this embodiment, paraxially collimated input light 375A and imperfectly collimated input light 375B are directed towards additional pinhole element 390B, where only light 375A may pass through, to be recollimated by additional recollimating element 320E. The paraxially collimated input light 375A may interact with the specimen within the sample volume 340, wherein the interaction between light 375A and the sample moieties may result in spectrally differentiable absorption of the light 375A. Light may scatter from interaction with the specimen in the sample volume to create scattered light 377B. Focusing element 320B may focus the light, which may include paraxially collimated output light 378A and scattered light 377B, towards pinhole element 390 wherein only light 378A (i.e., collimated light in the vertical direction) will pass through pinhole element 390, while the scattered light 377B will strike the pinhole element and be absorbed, scattered or reflected. The paraxially collimated input light 378A may thence be recollimated by recollimating element 320C. The resulting field of view 355 may thus be free of imperfectly collimated input light or scattered light.

The system 300 as shown in FIG. 3B is useful when on-axis collimation of the light entering into the sample volume is important, such as where plasmonic or diffraction elements are utilized to interact with an analyte in the sample volume 340, and the angle or polarization of light is an important factor of the interaction of the light with the plasmonic elements.

A system for blocking undesired light as described above may also be utilized as a subsystem in an optical path prior to light interacting with a sample, wherein there is not an additional system for blocking non-collimated or inadequately collimated light in an optical path subsequent to the input light interacting with the sample. Such a system may be useful where collimation of light is desired for use with a plasmonic projected diffraction element as described in Provisional Application No. 61/762,818, filed Feb. 8, 2013, which is incorporated by reference in its entirety. Such a plasmonic projected diffraction element may be associated with the sample volume 340.

Figure 4:
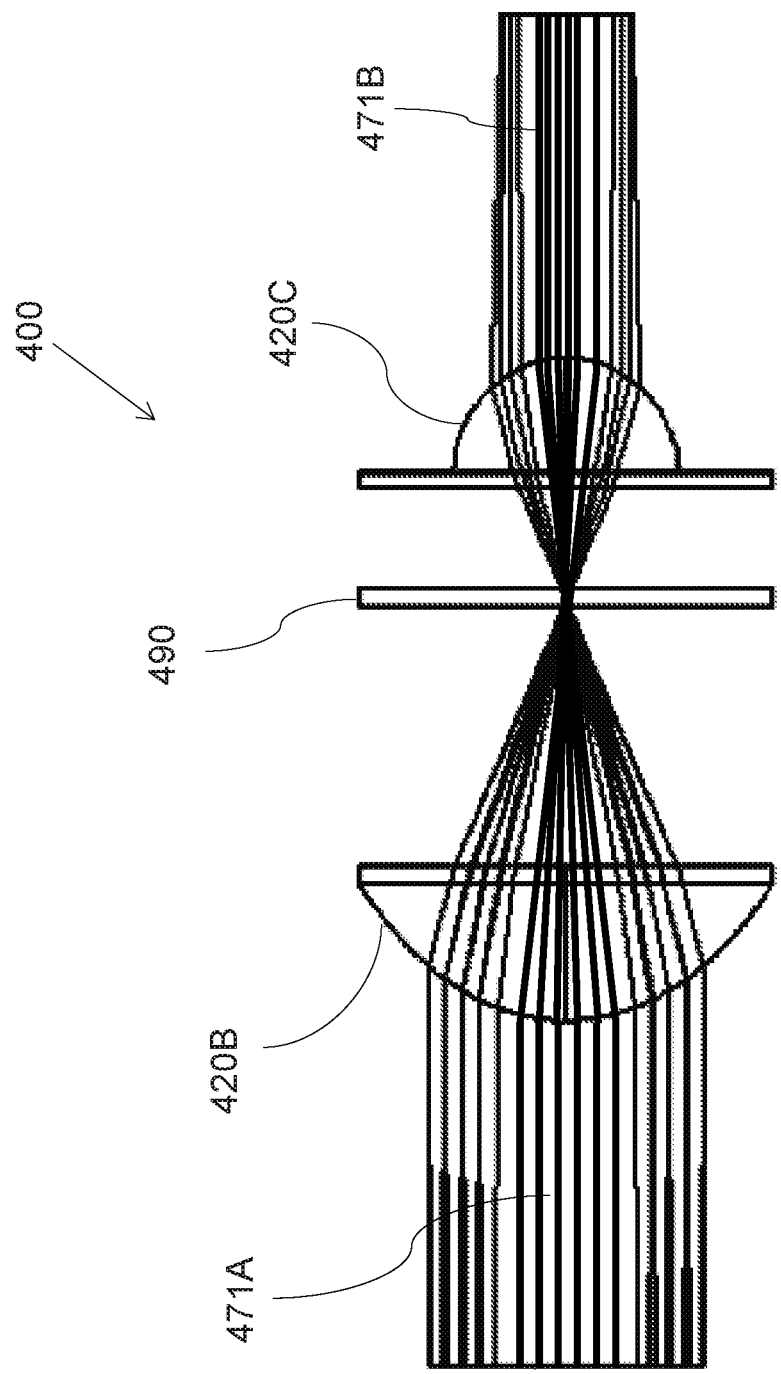
FIG. 4 depicts a side view of a spatial filter with magnification according to an embodiment of the present invention.
Figure 5A:
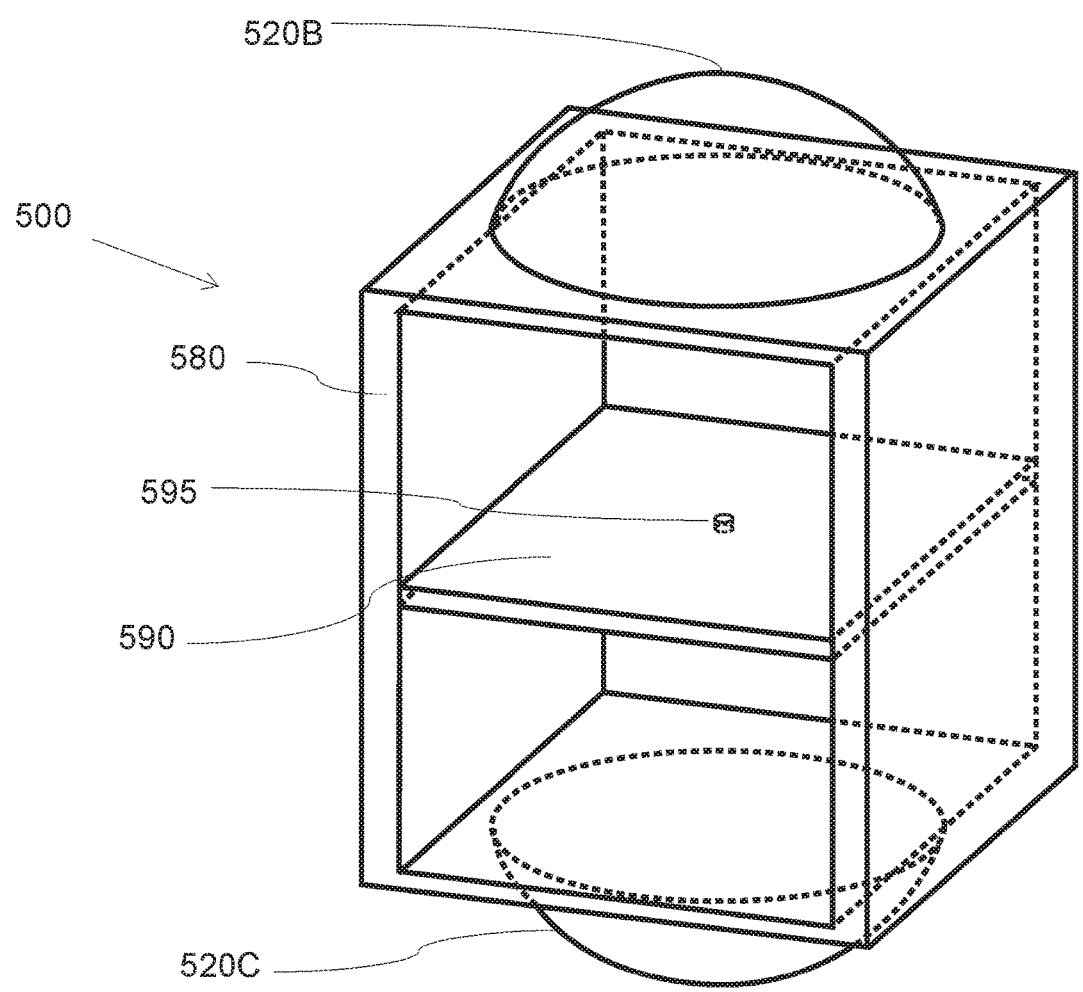
FIGS. 5A and 5B are perspective views of a spatial filter according to an embodiment of the present invention.

As described above, a combination of two optical elements with a pinhole functions as a spatial filter to block components of light that are not collimated in a desired direction. The combination of 320B, 320C and 390 and the combination of 320D, 320E and 390B, as shown in FIGS. 3A and 3B, both act as such spatial filters. The magnification factor of these spatial filters is 1 in these examples, but other magnification factors may be used by varying the focal length ratios. FIG. 4 shows a spatial filter 400 that has a magnification factor of less than 1 as light passes from the left to right. As shown in the figure, nominally collimated light 471A is focused by focusing element 420B before being directed towards pinhole element 490, and then being recollimated by recollimating element 420C to form collimated output light 471B. The focal lengths of focusing element 420B and recollimating element 420C can be seen to correspond to the size of the nominally collimated light 471A and collimated output light 471B, wherein the ratio is equal, and is also equal to the magnification. Thus, embodiments of the present invention include such a spatial filter with magnification and systems that include such a spatial filter. FIG. 5A depicts one embodiment of a self-aligned spatial filter system 500. This embodiment is a single monolithic device or a device consisting of multiple assembled pieces. A frame 580 supports and positions a pinhole element 590 with pinhole 595 positioned such that pinhole 595 is properly aligned to reject light that is not collimated in a direction perpendicular to the optical axis of the focusing element 520B. The pinhole element 590 may also be referred as a middle plate having a pinhole in this disclosure. The focusing element 520B and recollimating element 520C (or referred to as another focusing element) are positioned such that the focus of focusing element 520B and recollimating element 520C are substantially coincident with pinhole 595 for light which is collimated in the direction of the optical axis of the focusing element 520B and recollimating 520C. Focusing element 520B and recollimating element 520C are formed such that focusing element 520B and recollimating element 520C are aligned to share the same optical axis.

The self-aligned spatial filter 500 may be formed utilizing comolding techniques, such that frame 580 may be formed of a material different from that which may be used for focusing element 520B and recollimating element 520C, which may be made of the same material, or may be made of different materials.

This embodiment can be manufactured by the following manufacturing steps, for example. First, the framed structure comprising frame 580, the focusing elements 520B and 520C, and the middle plate 590 without a pinhole (i.e., the pinhole element 590 without a pinhole 595 formed therein) are manufactured by comolding techniques or assembly of respective pieces using appropriate materials. The focusing elements 520B and 520C are made of a material that is transparent to wavelengths of interest, such as visible light, UV light, IR light, etc. The middle plate 590 may be made of an opaque material such as metal or an absorbing dielectric material, or made of a transparent material having a metal layer or an absorbing dielectric material coated thereon.

The pinhole 595 can be made in middle plate 590 by irradiating the collimating element 520 with a collimated laser beam 570A of a sufficient energy to ablate a portion of the opaque material at the focal point of the collimating element 520. Alternatively, the opaque layer of the middle plate 590 may be subject to a photolithography process to form the pinhole. For example, a photoresist 598 may be coated on the opaque layer of the middle plate 590 by an appropriate coating method, and a substantially collimated exposing radiation 570A can be guided to irradiate the focusing element 520B to expose a portion of the photoresist 598 to form a resist pattern that defines the position of the pinhole 595. Thereafter, depending on whether a negative or positive photoresist is used, the lift-off technique or other thin film patterning technique is used to remove a portion of the opaque material at the focal point of the collimating element 520B to form the pinhole 595.

Thus, in the manufacturing method of this embodiment, substantially collimated light beam is used to find and define the focal point of the collimating element 520 in the plane of the middle plate 590 to form the pinhole 595 at the focal point, rather than assembling a pinhole element having a pinhole already formed therein with the collimating element. In other words, the pinhole is produced by a self-aligning step. If the middle plate is not laid exactly at the focal plane, the method described above would not locate a pinhole at the exact location of the focal point. Nonetheless, this methodology provides the best position for the pinhole to be made in the plane of the middle plate 590—i.e., a point in the plane of the middle plate 590 that optimally corresponds to the focal point. Moreover, any aberration or anomalies due to imperfection of the focusing element 520B can be reflected on the shape and position of the pinhole 595. For example, the shape of the pinhole 595 may take an oval shape instead of a circular shape if the corresponding aberrations are present in the collimating element 520B. Therefore, the spatial filter for reliably blocking light that is not collimated in the desired direction (the vertical direction in this example) can be manufactured by a simple and cost-effective manner.

The wavelength of the laser beam or exposing radiation used in the above-described exemplary manufacture method is preferably in the range of wavelengths for which the spatial filter is designed for use. For example, a doubled Nd:YAG laser operating at 532 nm, or a XeF excimer laser operating at 351 nm, may be used to make a spatial filter intended for selecting paraxially collimated light at a wavelength between 200 nm and 700 nm.

Other aspects, alternatives or modifications of this embodiment, some of which have been already discussed above are provided in the form of a list as follows:

(1) The middle plate (pinhole element) 590 may be formed of the same material as at least a portion of the frame 580, such as a moldable plastic, which may have light absorbing material such as carbon black contained therein. Alternatively a thin film may be formed on an optical material such as BK7 or other optical glass materials, wherein the thin film may be a metal, and may be a chromium oxide film, aluminum and or aluminum oxide, silver and or silver oxide, or other appropriate material. Alternatively, the pinhole element 590 may be formed of stainless steel, molybdenum, aluminum, or other metal, and may further comprise a film coating of chromium oxide or other material appropriate for light absorption. The metal may be deposited using electro-deposition, spray coating, ion beam, plasma or other types of sputtering, evaporating, chemical vapor deposition, physical vapor deposition, or other appropriate types of deposition. The thickness of the metal may be 100 nm, or may be of any thickness which provides sufficient blocking of imperfectly collimated and scattered light when used in a spectroscopic system.

(2) In some embodiments, an alternative method of forming—self-aligned spatial filter system 500 may begin with forming the portion of frame 580 which supports the pinhole element 590. This initial piece may thence have pinhole element without a pinhole, and may optionally have a photoresist layer formed on pinhole element 590. This combined subassembly may have a further molding process performed, wherein the side supports of frame 580 and supports for focusing element 520B and recollimating element 520C may be formed. The focusing element 520B and recollimating element 520C may be formed of the same material and at the same time as frame 580. Alternatively, focusing element 520B and or recollimating element 520C may be formed of different materials which may be formed with an additional molding step, or may be formed of a material, such as BK7 or other optical glass materials, and may be comolded into place as part of forming frame 580.

In a further embodiment, focusing element 520B or recollimating element 520C may be formed of different or the same materials, and may be bonded in place.

Figure 5B:
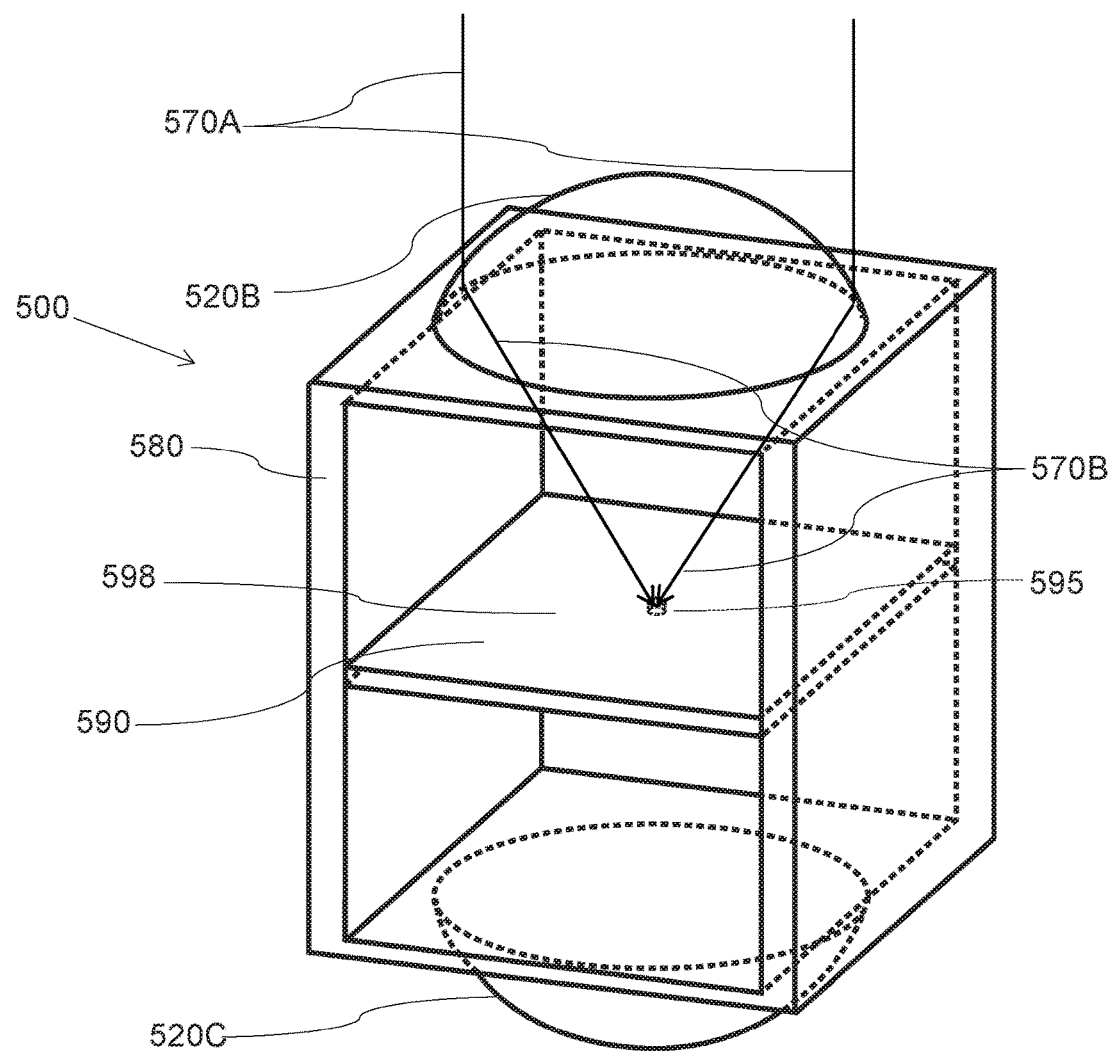

(3) In some embodiments, focusing element 520B or recollimating element 520C may be an off-the-shelf optical element or lens(es) which may be bonded in place. The optical centration of the off-the-shelf optical element or lens(es) may be imperfect, but the pinhole 595 will be formed by the optical element or lens(es) so as to be in line with the optical axis of the optical element or lens(es). The corresponding optical element (focusing element 520B if the pinhole 595 is formed by the recollimating element 520C, or recollimating element 520C if the pinhole 595 is made by the focusing element 520B) may have imperfect optical centration; the resulting system may either be manually aligned such that the optical centers are made to be axially coincident, or a shift in the angular output may be considered to be acceptable so as to obviate the need for alignment; such a shift in offset may thus require that the sensing device (not shown) may need to be larger than would otherwise be needed were the optical centers properly aligned. The manual alignment may be performed in several ways; the focusing element 520B or recollimating element 520C may be moved relative to the pinhole element 590 to properly align the two elements relative to each other. A collimated light source may be directed perpendicularly to the focusing element 520B or recollimating element 520C, while one of the focusing element 520B or recollimating element 520C or pinhole element 590 is moved so as to maximize the light which passes through the pinhole 595. The corresponding optical element which was not used to form the pinhole 595, or was not aligned to the pinhole 595 may be aligned to the pinhole by aligning the output of the combined system of focusing element 520B, pinhole element 590 with pinhole 595, and recollimating element such that the resultant beam is axially coincident with the center of the input collimated beam. After the alignment, it may be desirable to bond or clamp the optical elements or pinhole element in placed, using for example, UV curable adhesive. In some embodiments, it may be necessary to measure the focal lengths of the focusing element 520B and or the recollimating element 520C so as to set the distance between the aforementioned optical element and the pinhole element 590 such that the distance to the pinhole 595 is appropriately at the foci of the aforementioned optical elements. Although the use and methods of use of off-the-shelf optical elements is described here with respect to FIG. 5, the use and methods of such off-the-shelf elements may be utilized with any of the physical embodiments described herein.

(4) In some embodiments, particularly where focusing element 520B and or recollimating element 520C are formed of BK7 or other optical glass materials, pinhole 595 may be formed by ablation of a portion of pinhole element 590 which occupies the volume wherein pinhole 595 is desired. The use of the comolded BK7 or other optical glass materials permits the use of a high powered optical source which may be of a wavelength similar to the wavelength for which the—self-aligned spatial filter system 500 is intended to be used, and may be of a power level which may be needed for ablation of pinhole element in order to form pinhole 595. The use of a laser wavelength similar to the wavelength which is intended to be used provides for a focus with minimal chromatic aberration to form pinhole 595 of a size desired in pinhole element 590. In some embodiments, a frequency doubled or tripled Nd:YAG laser may be utilized to form a pinhole 595 in pinhole element 590.

(5) The focusing element 520B and or recollimating element 520C may be formed of an optical plastic such as PMMA (Poly Methyl MethAcrylate), polystyrene, polycarbonate, NAS (copolymer of 70% polystyrene and 30% acrylic), COP (Cyclic Olefin Polymer), COC (Cyclic Olefin Copolymer) such as Zeonex®, Acrylic, polyolefin Acrypet®, a methyl-methacrylate material such as Perspex®, or other appropriately moldable plastics useful for optical elements as known in the art. Focusing element 520B and or recollimating element 520C may comprise antireflection coatings, and the antireflection coatings may be on one or both sides of one or both focusing element 520B and recollimating element 520C. Such antireflection coating may be a simple one quarter wave magnesium fluoride coating or may be a more complicated multilayer dielectric antireflection coating. Focusing element 520B and recollimating element 520C may be simple spherical elements, or may be aspherical elements, or may be achromatic elements, or may be a binary lens element, or may be a Fresnel lens element, or one of focusing element 520B may be of one the above types of lens or another type of lens, while recollimating element 520C may be a different one of the above types of lenses, or may be a different type of lens.

(6) In some embodiments, the distance from the optical center of focusing element 520B may be strictly controlled with respect to the distances among the focusing element 520B, the pinhole element 590, and the recollimating element 520C, wherein the distances and any acceptable tolerances are a part of the mold(s) with which focusing element 520B, recollimating element 520C and frame 580 are formed. Similarly, the optical centration and alignment of the aforementioned elements may be set as part of the design of the mold(s) which form the aforementioned elements.

(7) As described above, as shown in FIG. 5B, collimated input light 570A which is aligned perpendicularly with respect to the planes of the focusing element 520B, pinhole element 590, and recollimating element 520C may be utilized to either ablate a pinhole in pinhole element 590, or to expose optional photoresist 598, such that focused light 570B will be focused so as to generate a pinhole of an appropriate size as set by frame 580, and the pinhole will be self-aligned to the optical axis of the lens with which it is formed. In order to insure that this pinhole is appropriately circular or takes other appropriate shapes, collimated input light 570A, in addition to being collimated and perpendicular to the aforementioned planes, should be centered with respect to the optical center of the focusing element 520B if collimated input light 570A is Gaussian in beam shape and similar in size to the focusing element 520B. Alternatively, collimated input light 570A may be uniform in intensity over a portion of focusing element 520B that is illuminated by collimated input light 570A, and centered with respect to the optical center of focusing element 520B, or collimated input light 570A may alternatively completely fill focusing element 520B with uniformly intense light.

(8) The size of the ablated pinhole may be set by utilizing a collimated input light of known power, and selecting the light power level and time so as to achieve a pinhole of an appropriate size based on previous experiments which determined the desired combination(s) of light power level and time. Alternatively, the size of the pinhole in the pinhole element 590 may be set by utilizing a feedback mechanism, wherein at least a portion of any light which passes through the pinhole as a result of the ablation process may be monitored with a photo-detector, and the collimated input light may be turned off when the light level passing through the pinhole reaches a desired level. The light that passes through the pinhole and is monitored by the photo-detector may be recollimated by the recollimating element 620C, and a portion of resultant light may be apertured, attenuated, beam split or otherwise reduced so as to be within the measuring capabilities of the photodetector.

(9) When photolithographic techniques for forming the pinhole in the pinhole element are utilized, the collimated input light 570A may be of a wavelength intensity and duration such that the photoresist layer 598 may be appropriately exposed so as to permit subsequent development of the photoresist which may be a positive photoresist in this embodiment, wherein further etching of a pinhole in pinhole element 590 is permitted by the aperture formed in the positive photoresist. In an alternative embodiment, a negative photoresist may be utilized, wherein the photoresist may be placed directly upon an optically transmissive portion of the frame 580, and a liftoff lithography methodology may be utilized, wherein after development, an "island" of hardened photoresist is left to form the pinhole, and a metal film is applied over the surface of the frame wherein photoresist had been applied, and the "island" of hardened photoresist is subsequently removed along with the metal which was deposited thereupon.

Figure 7A:
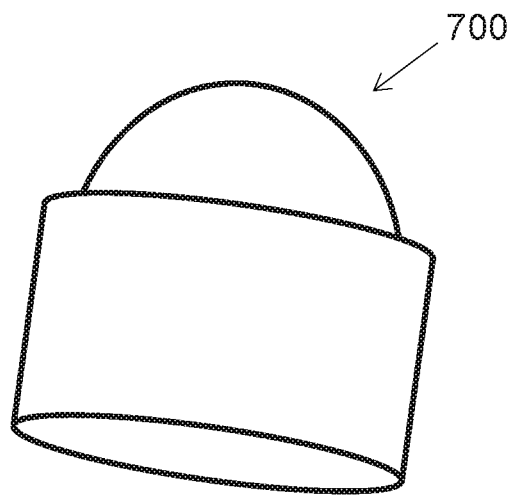
Figure 7B:
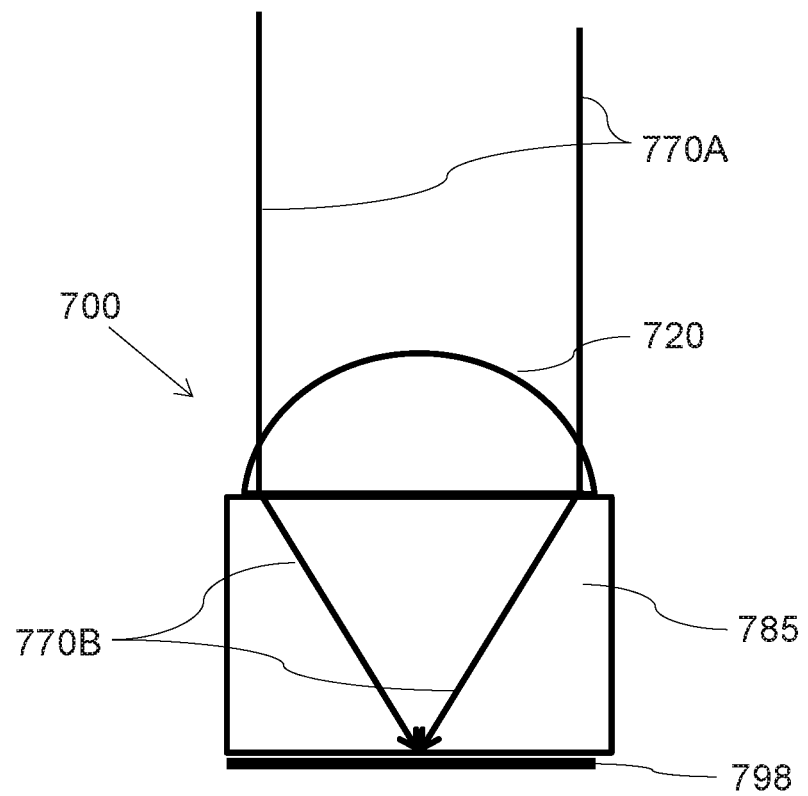
Figure 7C:
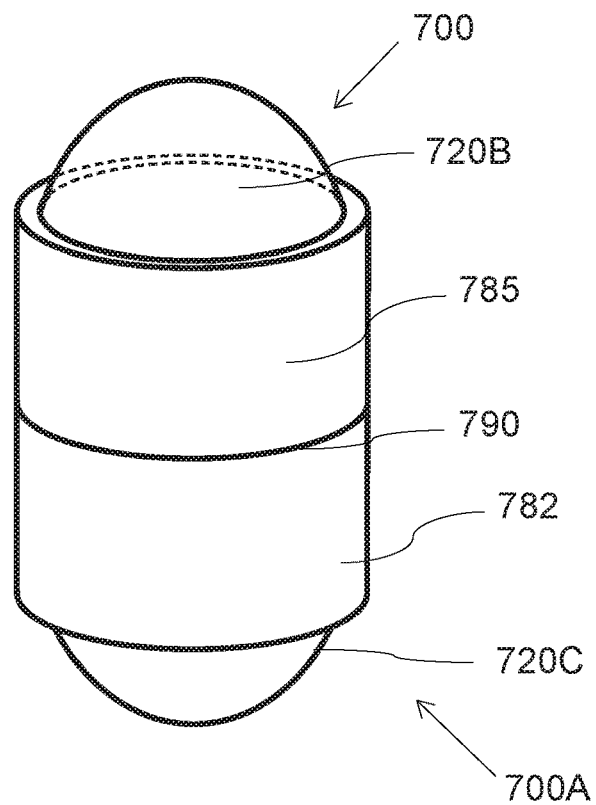

FIGS. 7A to 7C schematically depict another embodiment of the present invention. In this embodiment, an upper piece of block (solid substrate) 785 and a lower piece of block (solid substrate) 782 that is substantially identical to the block 785 in dimensions are put together with a pinhole element having a pinhole interposed therebetween (FIG. 7C). The upper block 785 has a collimating element (focusing element) 720B thereon, and the lower block 782 has a recollimating element (focusing element) 720C thereon. Each of the upper and lower blocks 785 and 782 may be made into a solid substrate by molding using the same die. Although the blocks 785 and 782 are shown as radially symmetrical cylindrical shape as a solid substrate, the shape of the upper and lower blocks that are supporting the respective focusing elements 720B and 720C may take a rectangular shape, a hexagonal shape, or any other shape.

In this disclosure, when a spatial filter is composed of two distinct pieces put together like the example shown in these figures, the upper block 785 together with the focusing element 720B and like structures may be collectively referred to as an "upper collimator" and the lower block 782 with the focusing element 720C and like structures may be collectively referred to as a "lower collimator" for ease of explanation.

Each of the blocks 785 and 782 may be formed integrally with the respective focusing elements 720B and 720C, which may be molded from plastic or glass or other optical materials. FIGS. 7A-7D show an example of a monolithically formed block in which the focusing element 720B and 720C is formed integrally with the respective supporting blocks 785 and 782.

In some embodiments, it may be desirable to utilize a lens element as part of the upper piece 700 or the lower piece 700A which has optical power in one dimension instead of two-dimensions or radially symmetric and behaves like a cylindrical lens element. Such a lens element may be desirable when it is desirable to retain as much light as possible, while maintaining collimation in one axis. This may be desirable when the light is to interact with a plasmonic element which is angle dependent in only one axis in certain designs.

FIG. 7B depicts a cross section of the upper piece 700, collimated input light 770A which is focused by focusing or recollimating element 720 to form focused light 770B in the block 785, which then forms a focus on the lower surface of the block 785, wherein it can expose photoresist 798, which may be a positive or negative photoresist as described hereinbefore, such that appropriate metallization may be applied to form a pinhole element. In other embodiments a metal film may be formed on the bottom surface of solid substrate 785 where photoresist 798 is shown instead of or in addition to photoresist 798, wherein the metal film forms a pinhole element. In some embodiments in which the solid substrate is formed from a glass or other optical material that is capable of withstanding the temperature needed for ablation, an ablation process may be utilized to remove a portion of the metal film, which forms the pinhole element, creating the pin hole in the pinhole element.

Figure 6A:
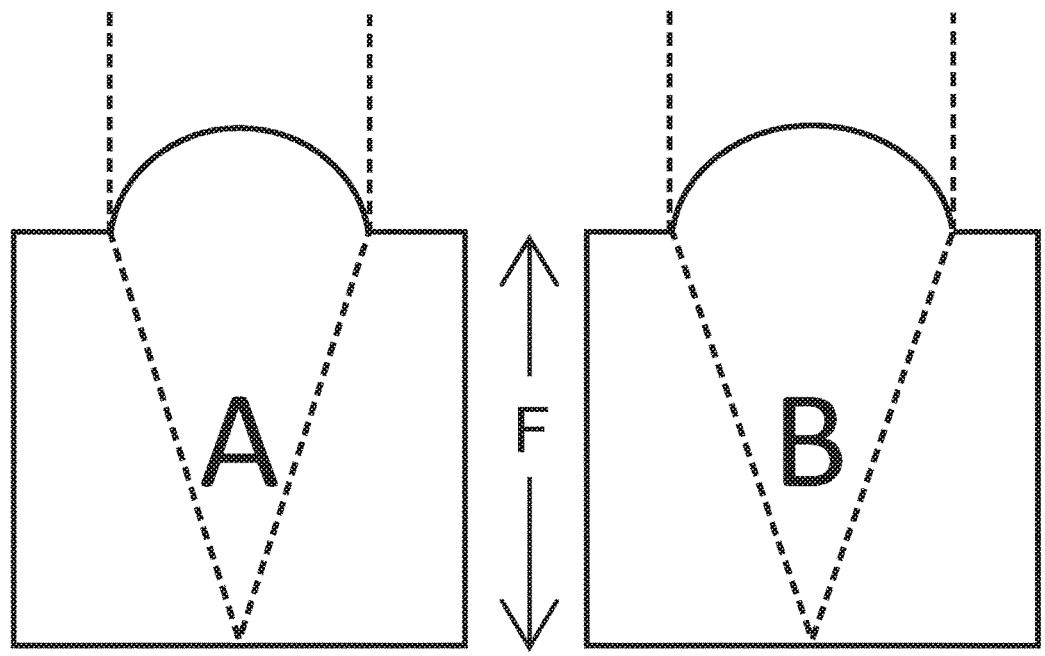
FIGS. 6A to 6V illustrate methods for manufacturing spatial filters according to embodiments of the present invention.

FIG. 7C depicts a perspective view of two identical molded half pieces, wherein the upper piece 700 is mated and bonded to bottom half piece 700A, wherein one of the half piece 700 and bottom half piece 700A also includes a pinhole element 790. FIG. 7D is a cutaway perspective view of this structure. The upper half piece 700 includes focusing element 720B with a solid substrate 785 corresponding to the focal length of focusing element 720B such that focus element 720B focuses at the interface between the upper half piece 700 and the bottom half piece 700A. The bottom half piece 700A may include recollimating element (another focusing element) 720C, which may have the same focal length as focusing element 720B, or may have a different focal length than focusing element 720B, and bottom solid substrate 782 corresponds to the focal length of recollimating element 720C such that the focus of the recollimating element 720C focuses at the interface between half collimator element 700 and bottom half collimator element 700A. The pinhole element 790 is fabricated on either the upper half piece 700 or the bottom half piece 700A prior to mating and bonding. Alternatively, pinholes can be fabricated on both the upper half piece 700 and the bottom half piece 700A, which will approximately align when the pieces are mated and bonded together. This alternative may be preferred to simplify manufacture at the cost of some performance. Some of the embodiments described above and additional embodiments of the present invention can be manufactured by the following process, for example. FIGS. 6A-6V are referred to for explanations of the manufacturing processes and the additional embodiments.

As shown in FIG. 6A, which shows side views, two substantially identical optically transparent cylindrical molded glass or plastic lens slugs, denoted as slug A and slug B, are prepared. The lensing surface can be any surface profile including, but not limited to, spherical, aspheric, binary (Fresnel), or composite. The bottom surface is nominally at the focal point for the particular design wavelength. The top lens surface and the bottom surface are transparent and of typical optical quality. The bottom surface is nominally perpendicular to the lensing surface's optical axis, and the cylindrical surface is coaxial with the optical axis in this example.

Figure 6B:
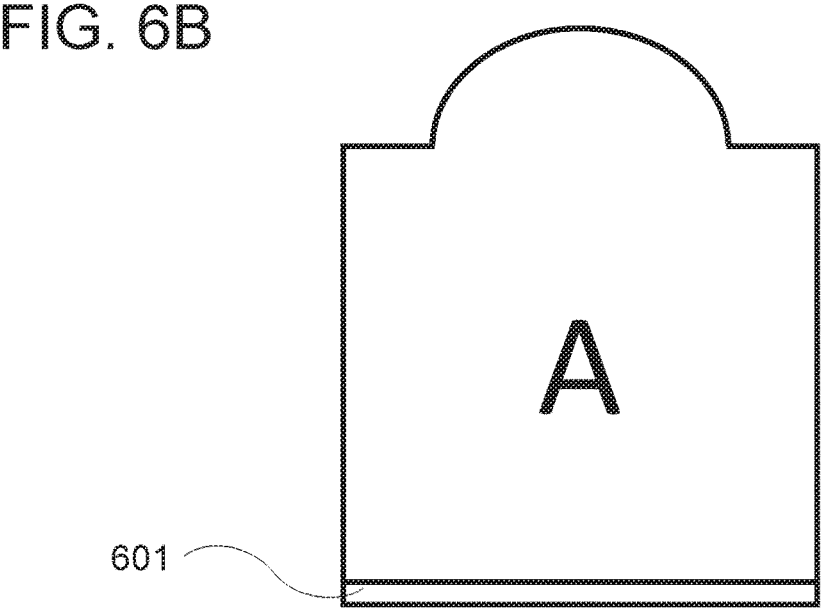

As shown in FIG. 6B, slug A's bottom surface is coated with a layer of metal 601 such as chrome, silver or aluminum via spray coating, electron beam or plasma sputtering metal deposition with thickness such that the metal is sufficiently optically opaque. If the slug is plastic, plasma sputter deposition or spray coating processes are preferred as their operating temperatures are lower and do not risk melting the plastic substrate. Alternatively, a separately manufactured metal plate or a transparent substrate having a metal layer formed thereon may be bonded to the bottom surface of the slug A. The slug B is not subject to this metal deposition/formation step.

Figure 6C:
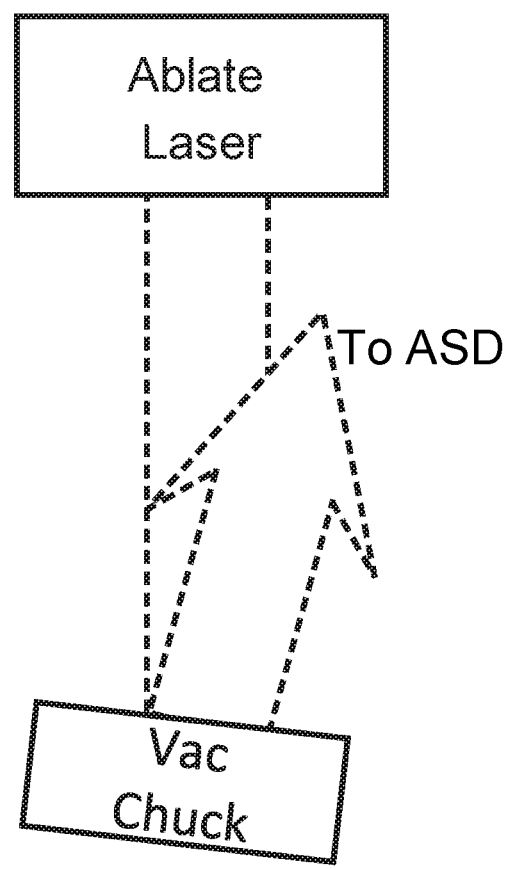
Figure 6D:
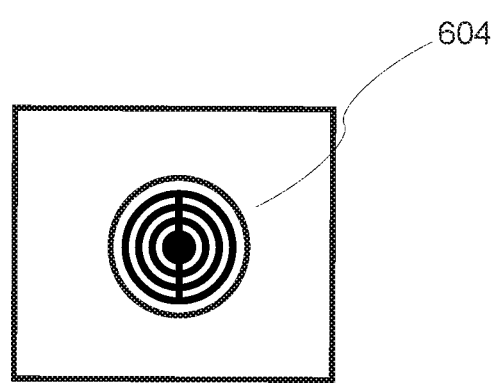

The slug A is then subject to laser ablation. FIG. 6C schematically shows a setup for performing laser ablation of the slug A. The ablation laser and a vacuum chuck for holding the slug A are prepared. FIG. 6D depicts a top view of the vacuum chuck. In order to ensure proper alignment of the optical axis of the laser beam with the surface of the vacuum chuck, the ablation laser is first operated in a low power mode for alignment purposes without the slug A being placed on the vacuum chuck. The ablation laser's alignment beam is incident upon a flat vacuum chuck that is polished to a reasonable optically degree such that the laser beam reflects. Upon reflection, the vacuum grooves 604 provide a "bulls-eye" type pattern, as shown in the top view FIG. 6D,—acting as an alignment reticle—and the reflection is monitored by an angle-sensing device (ASD) that is calibrated relative to the laser's optical axis. The vacuum chuck is tipped/tilted until the angle of reflection is minimized indicating that the vacuum chuck surface is normal to the ablation laser optical axis. The laser is then de-energized.

As shown in FIG. 6E, once the vacuum chuck is aligned, the slug A is placed centered on to the vacuum chuck with the flat side down, and vacuum is enabled, holding the slug A firmly to the chuck. Since the vacuum chuck has been aligned to be normal to the ablation laser's optical axis, the optical axis of the lensing surface of slug A is also nominally collinear to the ablation laser's optical axis because slug A's bottom surface is in contact with the vacuum chuck and slug A's bottom surface is nominally perpendicular to the lensing surface's optical axis. The ablation laser is fully energized, causing the metal coated on the bottom of Slug A to be removed, creating a pinhole 602, as shown in FIGS. 6F and 6G. The vacuum chuck has an escape thru-hole at its center to allow the laser energy to pass through to a beam-dump and/or to a monitoring photo-detector, and to allow the ablated material to escape. The pinhole size may be controlled by adjusting the laser power and/or dwell time and monitoring the intensity level of light that passes through the forming pinhole relative to a calibrated level with the optional photo-detector after being apertured, attenuated, beam split or otherwise reduced so as to be within the measuring capabilities of the photo-detector.

Figure 6H:
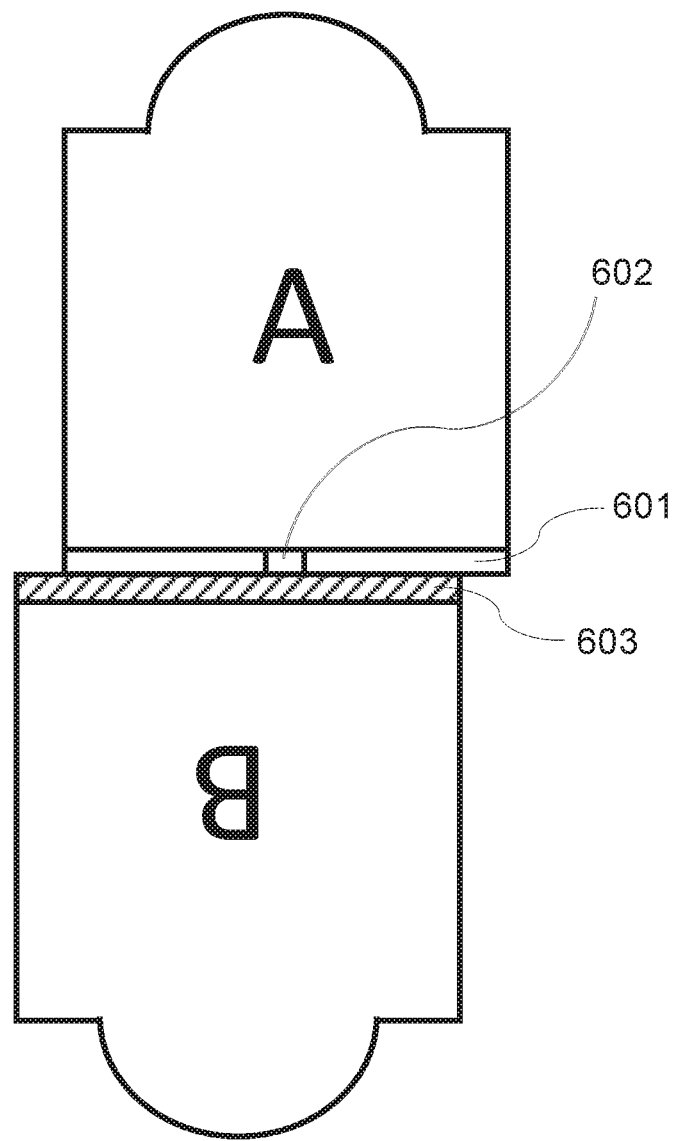

Thereafter, the slug B is attached to slug A having the pinhole formed thereon. Alternatively, two "slug A" parts may be attached together. As shown in FIG. 6H, a few drops of UV curable epoxy 603 are placed on the bottom of either slug A or slug B or on both (FIG. 6H shows an example of the epoxy 603 placed on the slug B). Slugs A and B are rubbed end-to-end to wick out excess UV epoxy and produce a thin & uniform epoxy layer 603. Depending on the initial amount and location of the UV epoxy 603, the pinhole 602 can be designed to be filled with the UV epoxy 603, or may be left as a void.

Figure 6I:
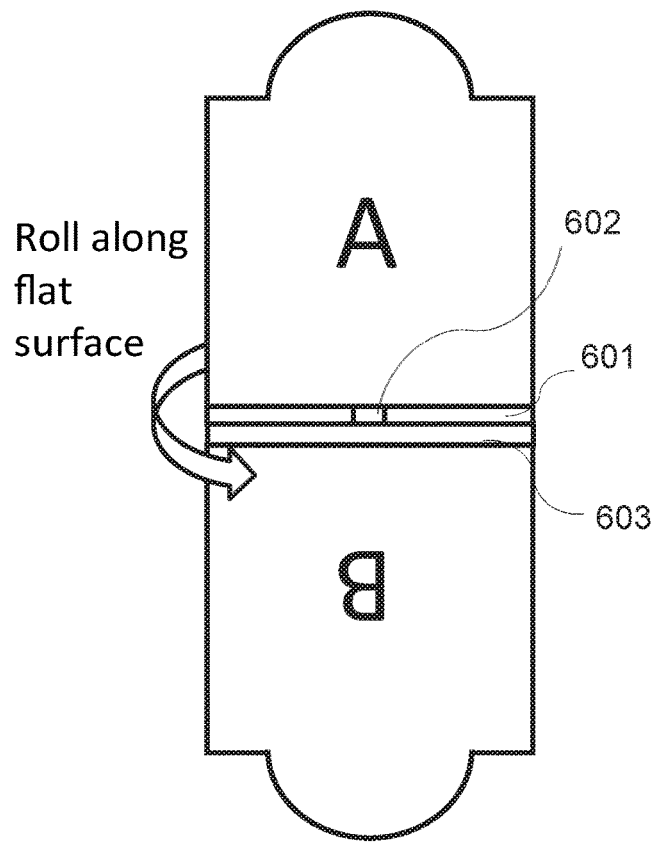
Figure 6J:
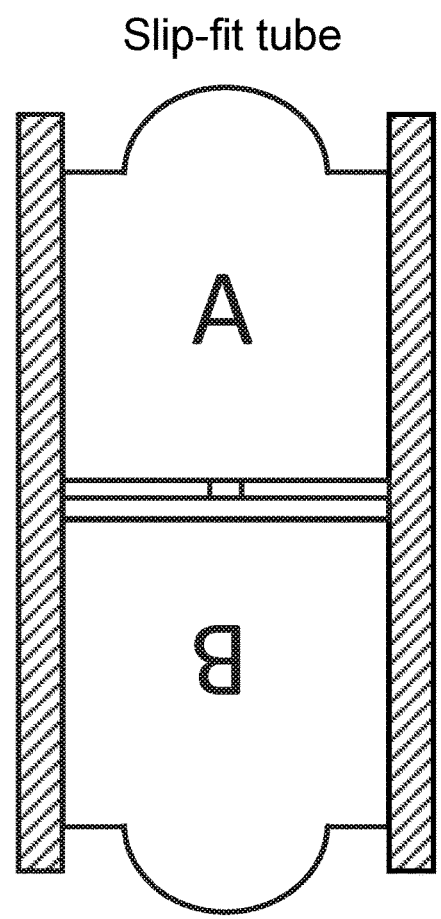

To align the slugs A and B properly, the edges of each lens cylinder are referenced relative to each other. This can be achieved by rolling the two cylinders along a flat surface until the slugs are concentric, as shown in FIG. 6I, or by placing the slugs into a slip-fit tube that holds the two slugs to be concentric, as shown in FIG. 6J. The slip-fit tube may also be lined with UV cure epoxy to permanently bond it to the slugs and strengthen the assembly. Although this scheme relies on the mechanical tolerances of the slip-fit cylindrical surfaces relative to the slug's optical axis, when an extremely high degree of precision and accuracy is not required as in many applications contemplated in this disclosure, this alignment produces sufficient performance in the resulting spatial filter.

UV light from a UV cure lamp is radiated to the resulting structure from the side of Slug B, for example, to cures the UV glue, bonding the two slugs together, producing a spatial filter module.

The UV curable epoxy 603 may be or may include commercially available ultraviolet (UV) curable inks marketed by Nazder Ink Technologies. The UV ink may be mixed with metallic powders to enhance the optical density of the spatial filter when the UV ink is applied to avoid the pinhole, hence improving the performance of the spatial filter.

Figure 6K:
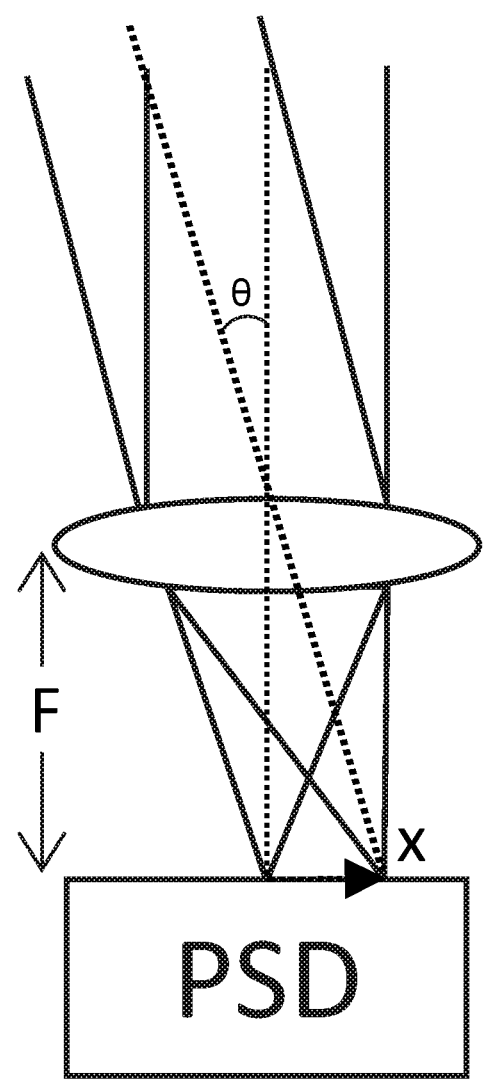

As the angle sensing device (ASD) mentioned above for aligning the surface of the vacuum chuck relative to the optical axis of the ablation laser beam, various techniques can be employed. A simple angle-sensing device is simply 2 pinholes spaced a long distance apart. Pinhole-1 forms the spot. The input laser beam is tipped/tilted until the spot passes through Pinhole-2. Light passes through Pinhole-2, reflects from the vacuum chuck and onto the backside of pinhole 2. The vacuum chuck is tipped/tilted until the reflected beam passes through both Pinhole-1 and Pinhole-2. The angular sensitivity is simply a function of the spacing (or throw) between pinholes and the ability of the human operator to visually resolve the centroid of the spot. An angle-sensing device similar to an autocollimator may also be used, which is schematically shown in FIG. 6K. A lens of focal length F is placed in front of a position-sensing detector (PSD) at a distance of F. In this configuration, if a laser beam strikes the lens relative to the lens's optical axis at angle θ, the beam will focus onto the PSD at a position related by the equation x=F*sin θ where x is a linear position. In this scheme, the beams lateral position relative to the lens is completely decoupled and the PSD's readout is directly proportional to the beam's angle relative to the lens.

Figure 6L:
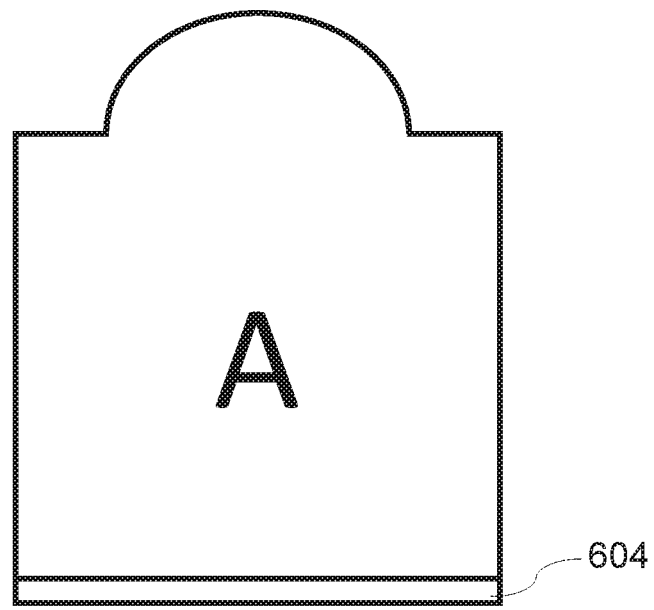

The above-described method utilizes laser ablation. Instead of the laser ablation of a metal layer, photolithography can be used to form a pinhole in an opaque layer, such as a metal layer. To do this, slugs A and B described above with reference to FIG. 6A are first prepared. Then, as shown in FIG. 6L, slug A's bottom surface is coated with a layer of negative photoresist 604 via spin or spray coating with thickness in the micro-scale. Slug B is not subject to the photoresist coating step.

Figure 6M:
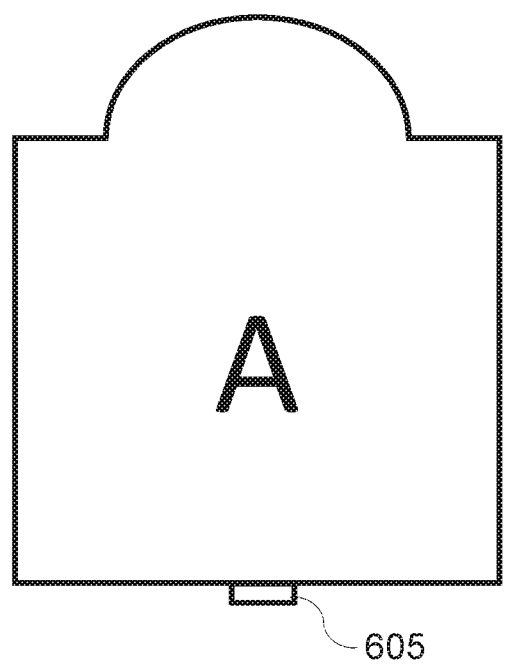
Figures 6N, 6O, 6P:
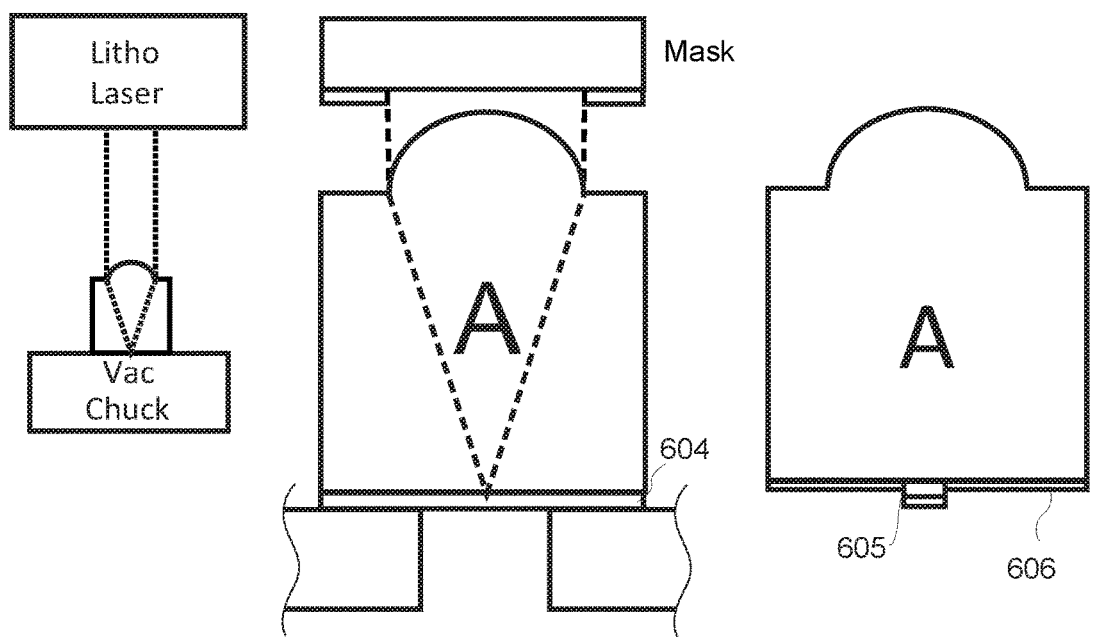

Then, slug A is subject to exposure with low energy Mine illumination to expose a select portion of the photoresist. An Mine source and a vacuum check configured similar to the vacuum chuck of FIG. 6E are prepared. After aligning the tip/tilt of the vacuum chuck relative to the source using the same angle sensing feedback discussed above, as shown in FIG. 6N, slug A is placed centered on to the vacuum chuck with the flat side down, and vacuum is enabled, holding the slug firmly to the chuck. As shown in FIG. 6O, a binary mask is placed over slug A to make sure that energy only transmits through the lens surface and not through the non-lens surface to avoid unintentionally exposing other regions of photoresist 604. The lithography system is energized, exposing the photoresist 604, causing the exposed areas to become insoluble in a developer. The vacuum chuck has a hole in it to prevent back-reflections from unintentionally exposing other regions of photoresist 604. The photoresist is post-exposure baked per the photo-resist manufacturer's recommendation, and developed. This process step results with pillar 605 of photoresist whose height is that of the original photoresist thickness, as shown in FIG. 6M.

The binary mask may not be necessary if the top side of slug A other than the focusing element 720B is metalized such that metal surrounds each lens clear aperture. This may also help prevent stray light from bypassing the pinhole when the spatial filter is in actual operation.

Subsequently, as shown in FIG. 6P, slug A's bottom surface is coated with a material 606, which may be a metal such as chrome, silver or aluminum or an absorbing dielectric material. The opaque layer may be applied via spray coating, electron beam, thermal, or plasma sputtering, physical vapor deposition, or other deposition techniques known in the art such that it is sufficiently optically opaque. If the slug is plastic, the opaque layer deposition temperature must be controlled to avoid melting the plastic substrate. Chemical mechanical polishing (CMP) or a solvent-liftoff process is employed to remove the metal "cap" from the photoresist pillar 605 on the bottom of the slug A.

In the case of CMP, the bottom of the slug A is subject to chemical mechanical polishing to grind off the metal cap above the photoresist pillar 605, planarizing the photoresist pillar 605 to match the height of the remaining metal, as shown in FIG. 6Q. The remaining portion of the photoresist pillar 605 may be removed by an appropriate wet or dry etching method if its presence is not optically desirable.

In case of the liftoff process, the slug A is placed in a solvent bath that may be enhanced by ultrasonic actuation to strip the photoresist pillar 605 and its encapsulating metal portion away. This process leaves a void where the photoresist pillar 605 was, as shown in FIG. 6R.

Thereafter, the slug A and slug B are attached in the same manner as described above to complete a spatial filter.

In the manufacturing process described above, the order of the photoresist coating and opaque layer deposition can be reversed if a positive photoresist is used instead of the positive photoresist. In such a case, a photoresist pattern is formed on the metal layer to expose a portion of the metal layer at or adjacent to the focal point of the slug A. The exposed metal layer is etched by an appropriate etching technique to form the pinhole in the metal layer. In this case, the exposure power and or duration must be increased to compensate for absorption through the opaque layer. Alternatively, the wavelength of light used to expose the photoresist may be selected to correspond to a spectral region where the opaque layer transmits light. Another alternative is to temporarily align slug A and slug B and expose the resist using slug B to generate the focused light for exposure. In this method, slug B may be replaced by a manufacturing fixture of similar optical performance that remains attached and aligned to the exposing illumination system.

Although the solid substrate 785 is used to construct the slug A in the above example, the upper piece having a collimating element and a pinhole element (without a pinhole) that will be subject to the above-described laser ablation or photolithography for the self-aligned formation of a pinhole may have a hollow structure. For example, a collimating element 720B may be separately manufactured or otherwise prepared, and the peripheral edge of the collimating element 720 B may be attached to a hollow frame having a cylindrical, rectangular or other appropriate shape using appropriate coupling and bonding structure and method. The hollow frame may be made of plastic, metal, or other appropriate structurally stable materials. A metal plate with an appropriate thickness or a glass or other transparent plate with a metal layer coated thereon may be separately manufactured or otherwise prepared, and may be attached to the other end of the hollow frame using appropriate coupling and bonding structure and method. This forms a structure constructed of a collimating element, a hollow frame, and a pinhole element (without a pinhole) as one piece adequate for the self-aligned pinhole manufacture using the laser ablation or photolithography, as described above. The bottom piece may be similarly constructed of a hollow structure with a recollimating element (but without a pinhole element), or made of a sold structure like the slug B as described above. After the pinhole is formed in the upper piece, the bottom piece can be aligned and bonded with the upper piece using appropriate aligning and bonding structure and method. FIG. 7L, which will be described in detail below, is an example of this structure.

The above-described processes can be applied to not only the manufacture of a single unit of the spatial filter, but also to the manufacture of multiple spatial filters at the same time with slight modifications. That is, the process can be multiplexed to make a plurality of units at the same time, thereby reducing manufacturing costs. In this multiplexed scheme, first, instead of a single piece of slug, such as slugs A and B as described above, a tile 607 shown in FIG. 6S or a tile 608 shown in FIG. 6T is formed from a molded substrate material. The tiles shown in these figures are equivalent to the slug A described above. The tiling can either be an array of single (or singlet) lens surfaces as shown in FIG. 6S, or may be sub-tiled as an array of multiple lenses (or lenslets) as shown in FIG. 6T. Each of the lenses or lenslets may have a different prescription (focusing power, surface profile, etc.) for its respective lensing surface. If the counterpart tile (equivalent to the slug B above) is to be used in a manner similar to the cases of slugs A and B as described above, then the substrate for the counterpart tile can be a mirror image of the tile to which it is coupled so as to match the optical prescriptions when tiles are bonded together.

Pinholes for respective lens or lenslets can be formed by the above-described methods without separating the tiles into separate pieces. Tile 607 or 608 with an opaque layer or a photoresist layer formed on its bottom surface is aligned relative to the ablation laser or lithography laser using the same scheme as described above. The vacuum chuck in this case must be large enough to accommodate the larger tiling.

In the case that the pinhole is directly formed into an opaque layer or metal film on the backside of the tile via ablation, the ablation beam need not be larger than each lens or lenslet surface. A stepper system can be used to position each lens or lenslet one at a time under the ablation laser source, and the laser can be energized and de-energized at each step. The vacuum chuck must have an escape thru-hole that corresponds to each lens or lenslet. Alternatively, a higher power ablation laser source can simultaneously illuminate more than one lens of lenslet through a suitable mask layer, or structured illumination can be used.

In the case that the pinhole is formed on the backside of the tile using lithography, the lithography illumination source can cover one or more lenses or lenslets at the same time. If the beam diameter of the exposing light source covers the entire array of lenses or lenslets, then the tile can be exposed all at once. If the lithography beam size does not cover the entire array of lenses or lenslets, then the beam can be sequentially positioned over each lens or lenslet, or a sub-array of lenses or lenslets depending on the beam size. In either case, a binary mask may be held in front of the lens or lenslet arrays to ensure that exposure light only enters through the lens surface(s) and not the non-lensing areas. After exposure, the above-described steps are followed to form the opaque layer and reveal the pinhole either via liftoff or CMP in the same fashion as described for the individual slug A except that processing equipment must be able to accommodate larger material.

A counterpart tile (equivalent to an array of the slugs B described above) can be attached and bonded to the tile with pinholes thus manufactured in a manner similar to that described for slugs A and B above. In performing alignment, however, instead of referencing relative to the cylindrical edge of the slugs, the tiles are either aligned relative to their edges, or they are actively aligned relative to fiducial alignment marks that can be formed on the respective tile substrate.

Figure 6U:
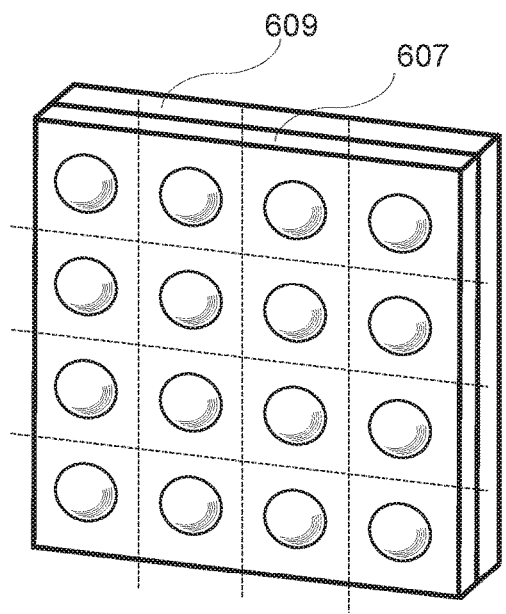
Figure 6V:
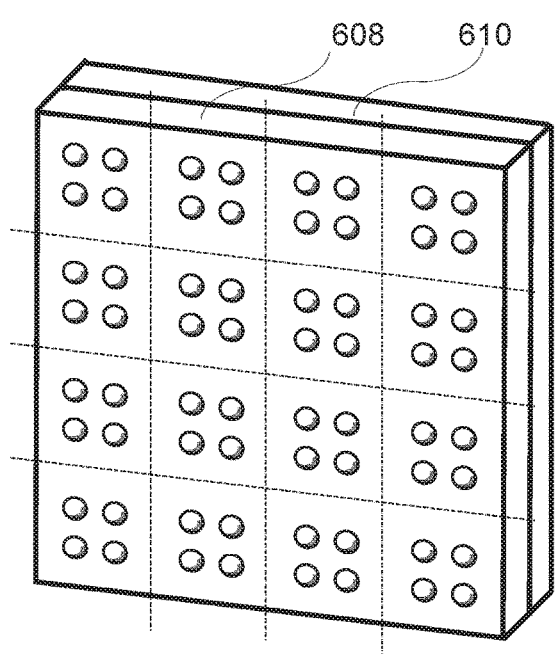
Figure 7D:
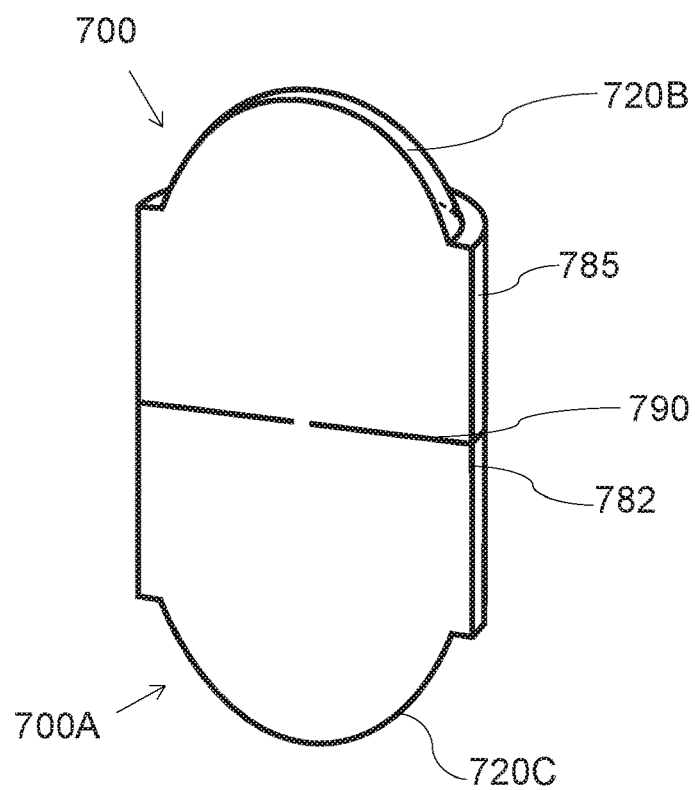

After the tile 607 or 608 with pinholes and the corresponding counter piece tile (609 or 610 as shown in FIGS. 6U and 6V) have been bonded together, thereby forming a tiled array of spatial filter modules, each individual spatial filter or a group of spatial filter can be diced apart using conventional dicing techniques forming a plurality of square slug-pairs. FIGS. 6U and 6V show examples of dicing lines with the dotted lines. After dicing, individual spatial filters or a group of spatial filters can be bonded into a square tube like the tube shown in FIG. 6J, to make the assembly more durable and easier to handle.

Alternatives and modifications as well as other aspects of the embodiments of the present invention, some of which have been discussed above, are provided in the form of a list, as follows:

(a) In some embodiments, a vacuum chuck may be utilized both to retain a top half collimator element or a bottom half collimator element, and to align the surface of the vacuum chuck such that the top or bottom half collimator, which is retained thereby, can be aligned perpendicularly to the laser beam used for ablation. The vacuum chuck may be polished to create a mirror surface which may reflect the input ablation laser beam, and a return beam may be monitored utilizing a beam splitter, which may reflect a portion of the return beam to a sensor such as a position sensitive detector (PSD), a quad photodiode, a CMOS image sensor, or any other appropriate sensing device. The vacuum chuck may then be adjusted in both theta and phi in order to insure that the vacuum chuck is perpendicular to the input ablation laser.

(b) In some embodiments, the input ablation laser may be operated at a power level which is utilized for ablation in creating pinholes while aligning the vacuum chuck when the beam is expanded to a size large enough so as to prevent damage to the vacuum chuck. In other embodiments, the input ablation laser may be operated at a reduced power during alignment, or may have only a portion of the input ablation laser beam directed towards the vacuum chuck, the remainder of the beam having been directed elsewhere by a beam splitter which may be an absorptive or reflective beam splitter. The ablation laser may be de-energized while parts are introduced to or removed from the vacuum chuck.

(c) In some embodiments, the vacuum chuck may have a hole beneath the location wherein the pinhole may be formed by ablation. A vacuum source may be utilized to draw away any ablated metal or other moieties so as to prevent deposition of any ablated material onto other optical surfaces which are part of the half collimator or bottom half collimator. In other embodiments, a vacuum source may be introduced via a tube into a volume above the pinhole, for example when a frame type half collimator structure as shown in FIG. 5 is utilized.

(d) In some embodiments, a vacuum chuck may have positioning pins or other registration features such that a single half collimator element or bottom half collimator element registered thereto may be centered under the input ablation laser beam. In other embodiments, the input ablation laser beam may be configured such that the input ablation laser beam may have a relatively uniform intensity level such that centering is not required.

(e) In some embodiments, a vacuum chuck may be sized to accommodate an array of half collimator or bottom half collimator elements. The vacuum chuck and the input ablation laser beam may be moved relative to each other if the size of the input ablation laser beam is insufficient to be utilized over the entire array of half collimator elements or bottom half collimator elements.

(f) In one embodiment, a negative photoresist may be utilized to form an "island" with diameter, x y location and thickness which can provide the pinhole. In some embodiments, the thickness of the island may be slightly thicker than the thickness of the desired pinhole element. The half collimator and the bottom half collimator may be brought into appropriate relationship of centration, planarity, and spacing with respect to each other. The relationship may be maintained by a lip that sets the spacing, centration and planarity. The spacing may be the same thickness as the thickness of the cured photoresist, or may be slightly thinner, such that the photoresist is slightly compressed, or may be slightly thicker, such that a small gap is left between the photoresist and the surface of half collimator to which the photoresist is not adhered. The lip may have one or more gaps such that a fluid may be introduced into the gap between the half collimator and the bottom half collimator. The fluid may be used to form an opaque film surrounding the "island" pinhole. The fluid may be a UV curable material, and may further comprise a light absorptive and or light reflective material, such as carbon black, gold or aluminum nanoparticles, and should wet both the half collimators and the photoresist. After introduction and uniform wetting, the fluid may be UV cured, bonding the half collimator and the bottom half collimator together.

Figure 7E:
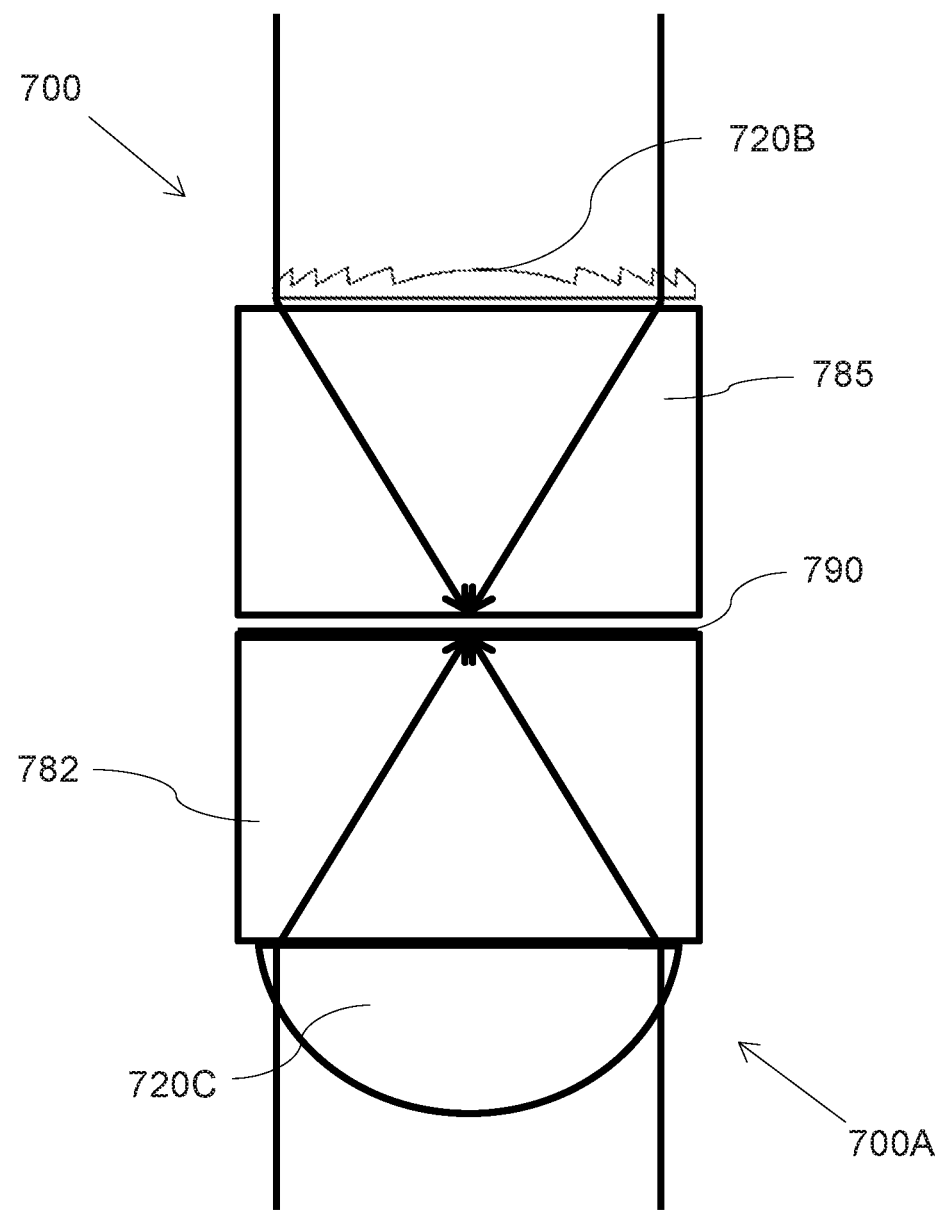

FIG. 7E depicts another embodiment, wherein an upper half collimator 700 and a bottom half collimator 700A are not identical molded pieces, as the half collimator 700 utilizes a Fresnel lens as the focusing element 720B, while bottom collimator utilizes a spherical or aspherical lens as the recollimating element (focusing element) 720C. In some embodiments, any of the optical elements as depicted in any of the embodiments herein may be a lens of any type, such as a spherical lens, an aspherical lens, a binary lens, a Fresnel lens, a biconvex lens, a plano-convex lens, a positive meniscus lens, a negative meniscus lens, a plano-concave lens, or a biconcave lens, or may be any of the above in combination with any other lens or lenses. Solid substrate 785 and bottom solid substrate 782 correspond in length to the focal lengths of focusing element 720B and recollimating element 720C respectively, and the pinhole element 790 is depicted as being fabricated upon the bottom half collimator 782 in this example. The use of a Fresnel lens permits the assembly to be placed closer to the sample volume. In some embodiments, it may be desirable to form both focusing element 720B and recollimating element 720C with Fresnel lenses or it may be desirable to form the recollimating element 720C with a spherical lens, while focusing element 720B may comprise a Fresnel lens.

In some embodiments, the top half collimator 700 and the bottom half collimator 700A may be aligned using optical techniques prior to or as part of bonding together the top half collimator 700 and the bottom half collimator 700A. In other embodiments as shown in FIG. 7F-7K, for example, mechanical alignment methods may be used to align the top half collimator 700 and the bottom half collimator 700A.

FIG. 7F depicts another embodiment wherein the bottom collimator solid substrate 782 has a diameter larger than the solid substrate 785, and the bottom half collimator 700A also includes a retaining lip 786, which centers the top half collimator 700 relative to the bottom half collimator 700A. In this example, a pinhole element 790 is formed on the bottom surface of the top half collimator 700 which is formed with a spherical lens for focusing element 720B and a solid substrate 785, while the bottom half collimator is formed with a Fresnel lens for recollimating element 720C.

FIG. 7G depicts another embodiment wherein the solid substrate 782 of the bottom half collimator 700A can have a short vertical dimension. The bottom half collimator 700A has a hollow shell which acts as a support/spacer between recollimating element 720C and the top half collimator element 700, whilst retaining lip 786 is utilized for centration of the bottom collimator relative 700A to the top half collimator 700 and for attachment and bonding of the top and bottom collimators 700 and 700A together. In this example and other embodiments described herein, when there is an air space between the focusing element and the pinhole element, the vertical gap of the space can be shortened significantly as compared with cases where the space is filled is dielectric material, such as about a half of the corresponding space for collimator element 700, to account for the difference in refractive index of air and the material otherwise utilized for the bottom solid substrate 782. This configuration has the advantage of a greater optical power due to having two surfaces with changes in refractive index.

FIG. 7H depicts a three-part system wherein top half collimator 700 and bottom collimator 700A are formed as having the same diameter at solid support 785 and bottom solid support 782, respectively. As shown in FIG. 7H, a retaining ring 787A is utilized to retain centration of the half collimator 700 and the bottom collimator 700A.

FIG. 7I depicts a four-part system, wherein recollimating element 720C is not molded as part of bottom solid substrate 782, but is instead a separate element which is retained and centered by retaining ring 787B, which in this embodiment is longer than bottom solid substrate 782, and slightly overlaps recollimating element 720C to provide retention and centration between recollimating element 720C, bottom solid substrate 782, and half collimator 700. In a further extension of this embodiment, both of the half collimators can be constructed in the same manner. For example, a separate optical element, which comprises the focusing element 720B, can be retained by another retaining ring similar to the ring 787B relative to the top solid substrate 785, wherein these retaining rings are interleaved to provide alignment without mutual interference. Alternatively, one of the retaining rings can be made shorter than the other retaining ring such that interference does not occur.

Another embodiment is depicted in FIG. 7J, which shows a three-part system wherein bottom solid support 782 has two retaining lips 786B and 786C, one for centration of the bottom half collimator 700A to the half collimator 700, and one to center the recollimating element 720C relative to the bottom solid substrate 782. In addition, the focusing element 720B can be retained by retaining lips formed on the top solid support 785 similar to the lips 786, wherein one of the retaining lips is short so to prevent interference with double retaining lip structure 786 of the opposing structure.

Another embodiment is depicted in FIG. 7K, which shows a three-part system wherein bottom solid substrate 782 has two retaining lips 786D, but unlike FIG. 7J, bottom solid substrate 782 is actually a hollow cylindrical structure, which acts as a spacer between the half collimator 700 and the recollimating element 720C. The cylindrical structure 782 is hollow inside and supports the peripheral edge of recollimating element 720C. In this case, lens 720C is supported by bottom solid substrate 782 above a volume of air.

In another embodiment as depicted in FIG. 7L, both the focusing element 720B and the recollimating element 720C are supported by hollow cylindrical structures 785 and 782 (or any other hollow structures), respectively, to define the respective spaces and support the focusing element 720B and the recollimating element 720C, respectively, relative to the pinhole element 790, such that air spaces with associated refractive index changes are present, allowing focusing element 720B and recollimating element 720C to be higher power optical elements, thus reducing the size of the spatial filter module. The top cylindrical structure 785 and the bottom cylindrical structure 782 are respectively bonded to the respective peripheral edges of the focusing element 785 and the recollimating element 720C by appropriate structures and adhesives.

To form this structure, the top cylindrical structure 785 is first attached to the collimating element 720B and the pinhole element 790 (with a pinhole not yet formed) to construct the top half collimator 700, and the laser ablation or photolithography is performed on the top half collimator 700 to form a pinhole in the pinhole element 790 in a self-aligned manner. The top half collimator 700 with the pinhole is then aligned and bonded to the bottom half collimator 700A. The attached FIG. 7L depicts a single retaining ring 786E, which aligns the top half collimator 700 and the bottom half collimator 700A. If the focal length of the focusing element 720B and the recollimating element 720C are the same, then the identical parts may be utilized for half collimator 785 and bottom half collimator 782.

Furthermore, the pinhole element 790 of FIG. 7L may be fabricated using of any one of the other processes described above. For example, the focusing element 720B and the cylindrical structures 785 and 782, and a pinhole element 790 (with a pinhole not yet formed) may be held in place by retaining ring 786E while a pinhole is formed in pinhole element 790 using self-aligned techniques as described above.

In further embodiments, the focal length of focusing element 720B and recollimating element 720C may be different, requiring different lengths and thus different parts for top half collimator 785 and bottom half collimator 782. In yet further embodiments, one of the top half collimator 785 and the bottom half collimator 782 may have an additional lip similar to that shown in FIG. 7G so as to serve both the function of alignment between the half collimator elements and be half collimator element.

In the embodiment as depicted in FIG. 7L or like embodiments of the present invention, after retaining ring 786E is put into place to center the top half collimator 700 and the bottom half collimator 700A, the top and half collimators 700 and 700A are pushed fully together such that they are fully in contact with pinhole element 790. An adhesive, which may be UV curing adhesive or any other type of adhesive, may be utilized to bond retaining ring 786E to both the top half collimator 700 and the bottom half collimator 700A. This bonding method may be used for any embodiments described herein where direct bonding of optical surfaces is not needed or not possible, and can be utilized for any of these systems if the refractive index changes which occur when transitioning from plastic or glass to air and back again are not disadvantageous.

In some embodiments, wherein refractive index changes may be undesirable, it may be desirable to utilize a UV curable index matching adhesive, which may be applied both the lower face of the top half collimator 700 and the upper face of bottom half collimator for a system such as one shown in FIG. 7J. In order to insure proper alignment and optical distance between the top half collimator and bottom half collimator, a set of registration stops 789 as shown in FIG. 7M may be utilized to insure a desired fixed spacing between the top half collimator and the bottom half collimator at effectively all positions at the periphery of the half collimator 700 and bottom half collimator 700A. Extra adhesive may be applied to the mating surfaces, and excess adhesive may be pushed out through grooves in retaining lip 787C. This bonding method may be used for any of the embodiments described herein where direct bonding of optical surfaces is desirable or required, and could be utilized for any of these systems if the refractive index changes which occur when transitioning from plastic or glass to air and back again are disadvantageous. If the glue for bonding these elements would interfere with the optical performance of the system, the glue or other appropriate bonding method or structure should be applied at the perimeter of the respective elements to avoid or minimize such interference.

As described above, arrays of spatial filters may be manufactured by the manufacture methods disclosed herein. Costs associated with production of individual spatial filters can be reduced by creating the arrays and then dicing or otherwise separating the arrays into sub arrays or individual spatial filters. An array of un-diced spatial filters may also be used as it is in certain applications, such as where different light wavelengths are utilized in different portions of an array of different irradiation areas. In such a case, individual spatial filters within the array may be optimized for different wavelengths. Moreover, when an area to be irradiated is more easily addressed with an array of sources than with a single large source, such an array or an array of identical spatial filters may be made in accordance with the present disclosure and utilized.

In the embodiments wherein different wavelengths are utilized for different locations in an array, and the focal lengths are "tuned" to accommodate any chromatic aberration, both the top half collimator and the bottom half collimator may need to have the same chromatic aberration "tuning" such that when mated into a non-collimated light blocking system, each position may be "tuned" for the same wavelength.

Figure 8A:
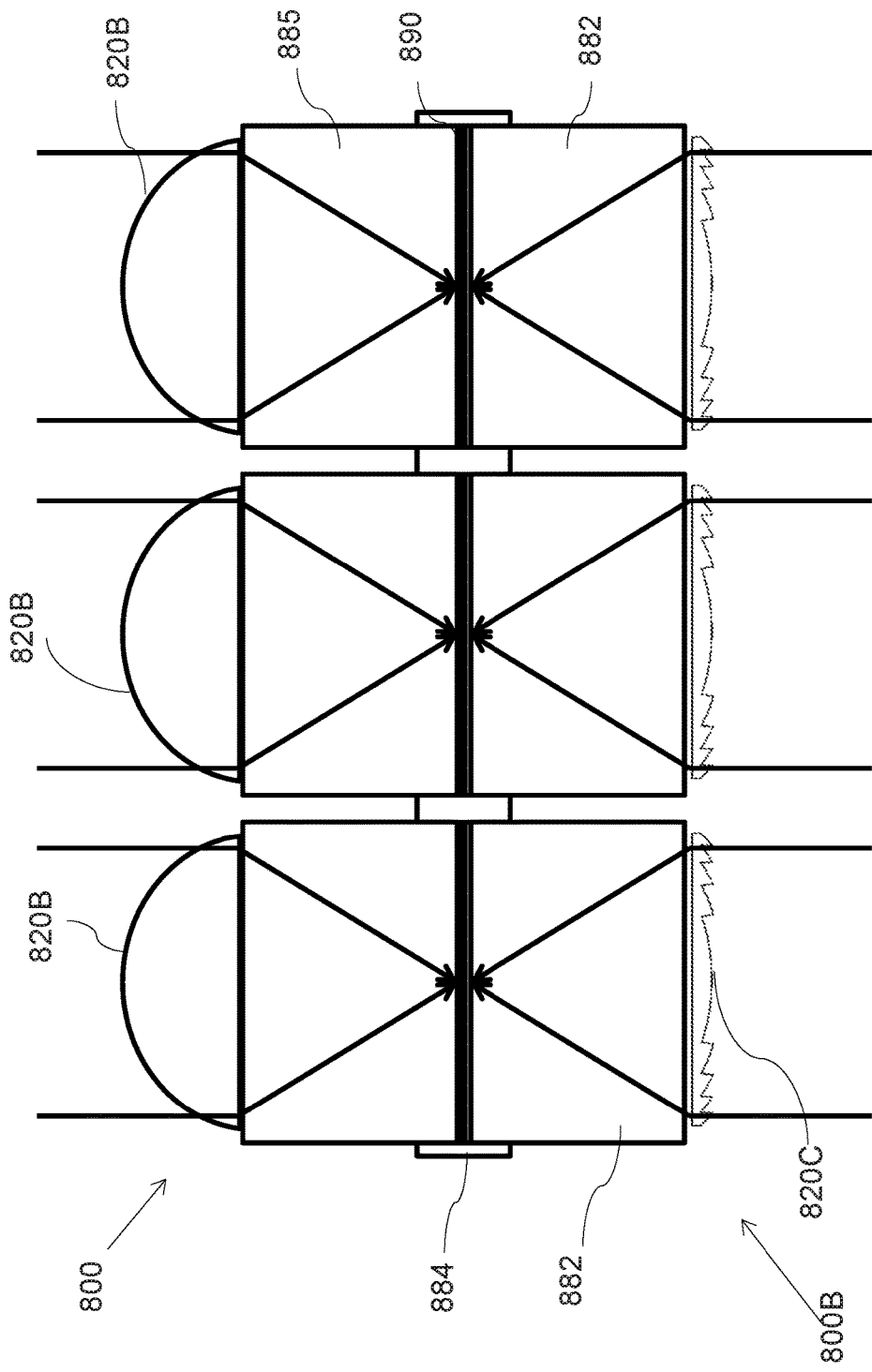
FIGS. 8A to 8F illustrate embodiments of spatial filters or spatial filter arrays according to embodiments of the present invention.

FIG. 8A shows an example of array configurations in the manufacturing process. As shown in FIG. 8A, first, a plurality of top half collimators 800 (referred to as a "top array") is fabricated with focusing elements 820B in association with solid substrates 885, while a plurality of bottom half collimators 800B (referred to as a "bottom array") is fabricated with recollimating elements 820C associated with the bottom solid substrates using the manufacturing methods described above. Pinhole elements 890 may be formed on one or associated with one of the top half collimators and the bottom half collimators, and pinholes may be formed in pinhole elements 890 by the methods described above. The top array 800 and the bottom array 800B thus manufactured are aligned and coupled using a retaining ring array structure 884 to simultaneously align and bond the top half collimator and the bottom half collimator.

Although retaining ring array structure 884 is shown as not registering against any stop in the z axis (along the optical axes) in FIG. 8A, a physical registration stop or structure similar to that disclosed and explained in association with FIGS. 7A-7M may be utilized to insure that respective components of the spatial filters are properly aligned.

Figure 8B:
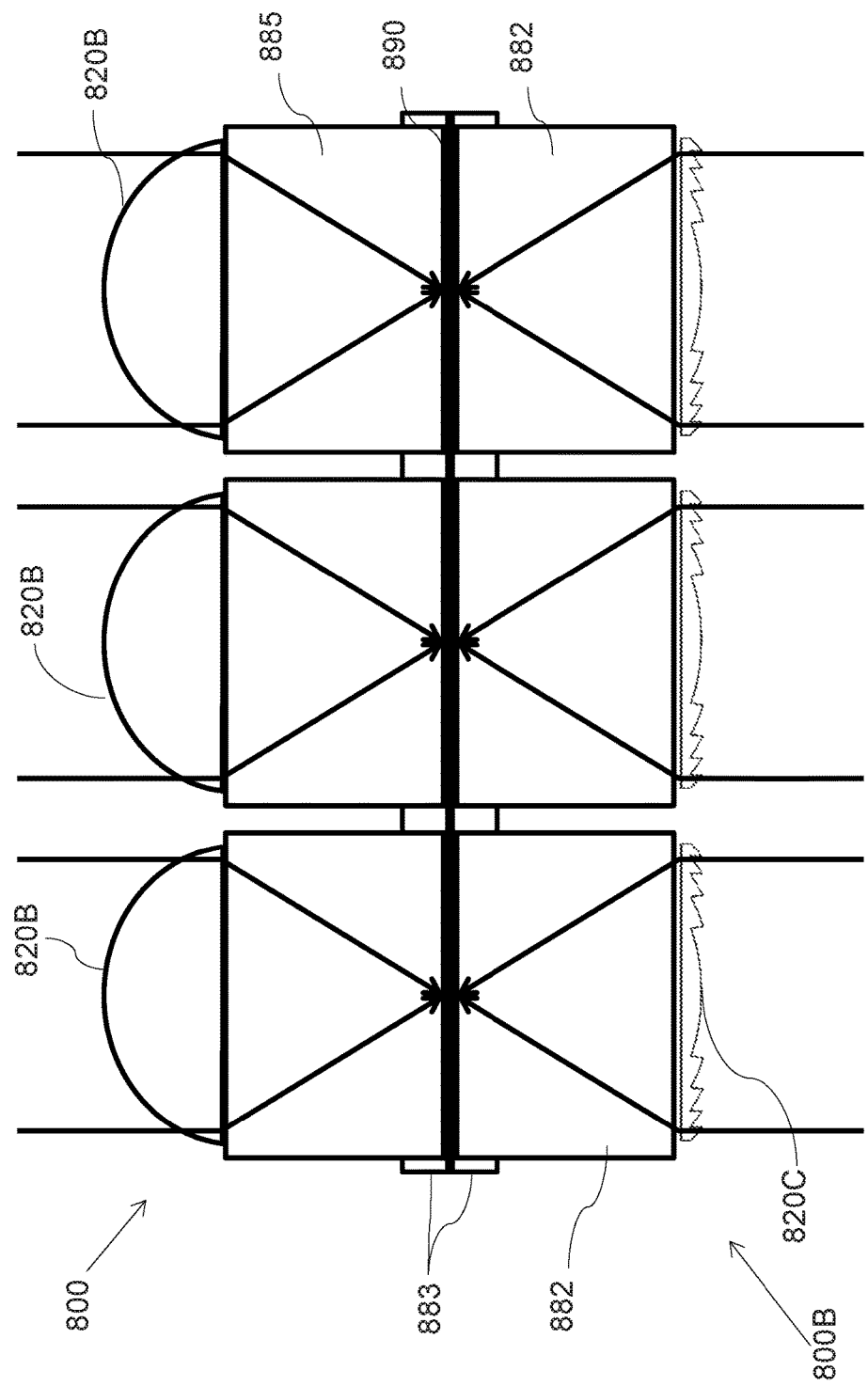

In other embodiments as depicted in FIG. 8B, an array of half collimators 800 and an array of bottom half collimators 800A are fabricated with sprues 883 interconnecting the top half collimators and the bottom half collimators, respectively. The sprues may be molded connected to the top solid substrates 885 and the bottom solid substrates 882 respectively to create arrays of half collimators 800 and bottom half collimators 800A associated with focusing elements 820B and recollimating elements 820C respectively, and pinhole elements 890 may be associated with one of the half collimators 800 or the bottom collimators 800A.

In some embodiments, the sprues 883 depicted in FIG. 8B may be retained, and may serve to insure coaxiality of half collimators array 800 and bottom half collimator array 800A. In other embodiments, the sprues may be cut broken diced, or otherwise prevented from continuing to hold together the half collimator array 800 and or the bottom half collimator array 800A. Separated half collimator array 800 elements and or bottom half collimator 800A elements may be utilized as individual half collimators or bottom collimators using any of the methods described herein.

Figure 8C:
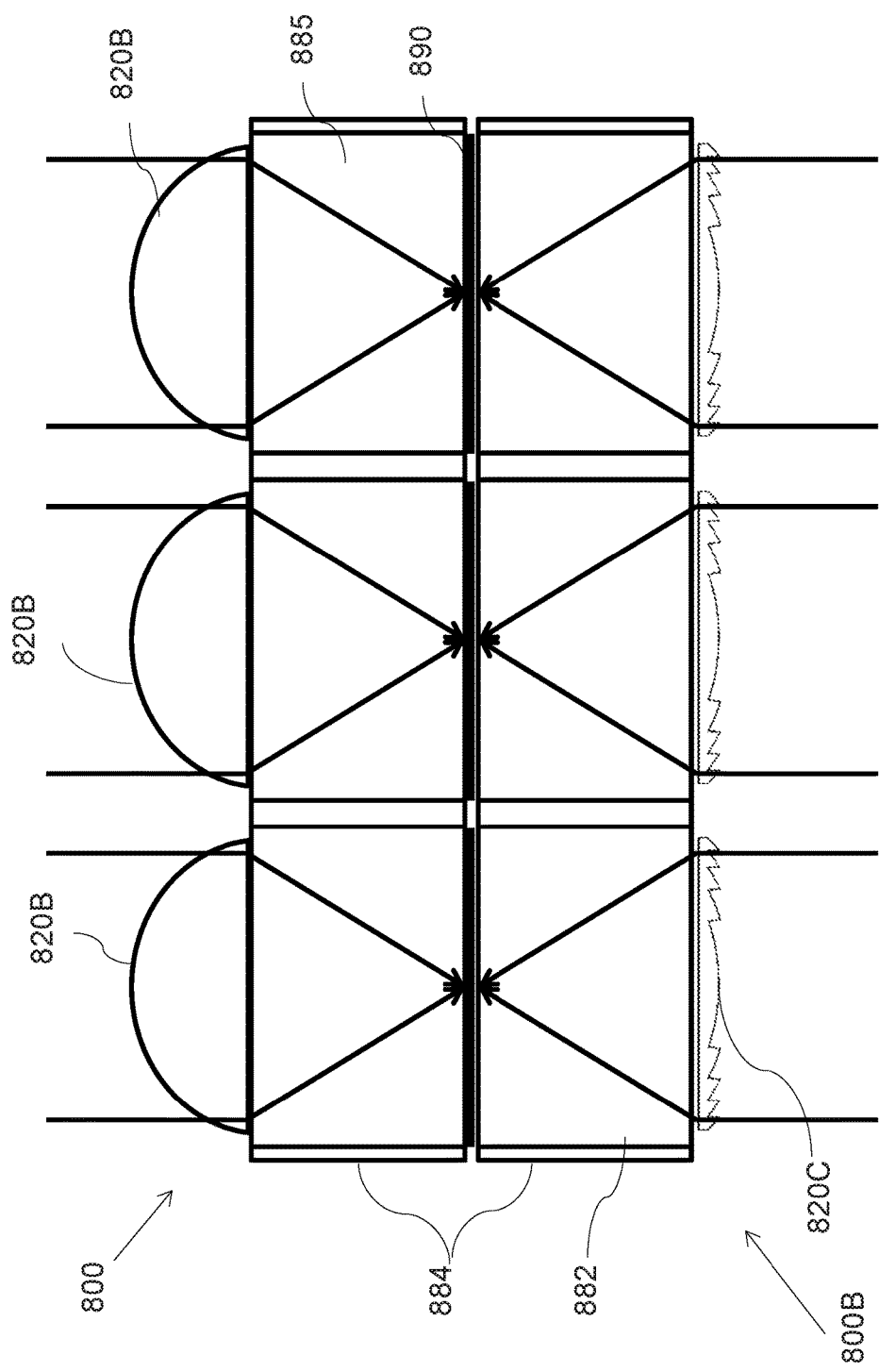

FIG. 8C shows another embodiment of the present invention. As shown in FIG. 8C, arrays of half collimators 800 and arrays of bottom collimators 800A may be fabricated utilizing a comolding process wherein arrays of half collimator elements and bottom collimator elements may be molded prior to or after molding retaining ring array 884, which may serve to align and hold the individual top half collimators and/or individual bottom half collimators relative to each other, thus holding the position of the respective solid substrates 885, bottom solid substrates 882, focusing elements 820B and recollimating elements 820C, as well as pinhole elements 890 which are associated with one of the half collimator or bottom half collimator elements.

Figure 8D:
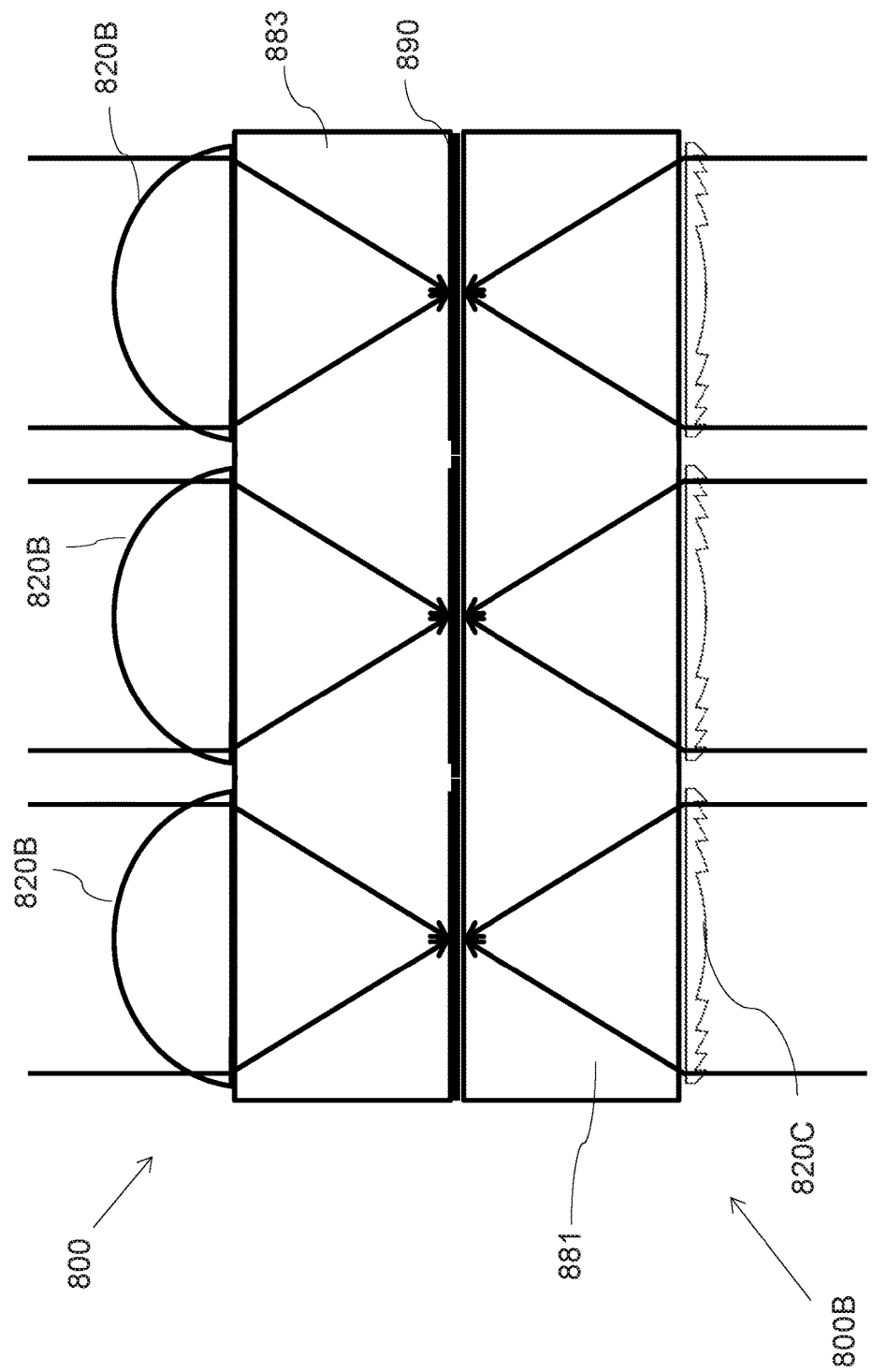

FIG. 8D shows another embodiment depicting a top half collimator array 800 and a bottom half collimator array 800B wherein pinhole element 890 covers the entire surface of one of the top half collimator elements and the bottom half collimator elements, and wherein a pinhole is formed in association with each pair of focusing element 820B and recollimating element 820C. The focusing elements 820B may be associated with a planar solid substrate 883 while the recollimating elements 820C may be associated with a bottom planar solid substrate 881.

Figure 8F:
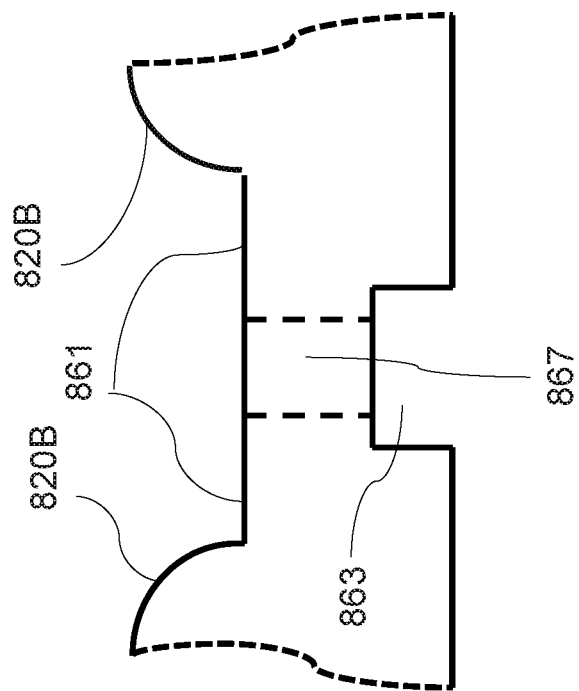
Figure 8E:
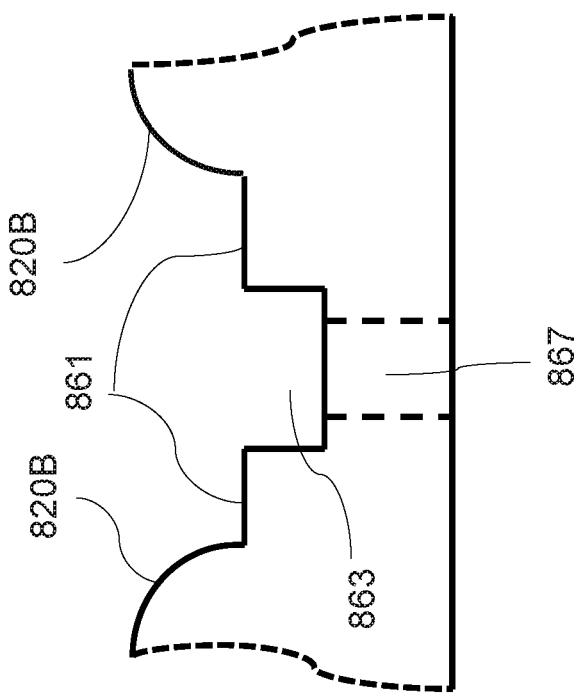

FIG. 8E depicts a view of a half collimator array with a notch 863 molded between the focusing elements 820B such that when cut or diced, a removed volume 867 will not remove material past shoulders 861, protecting both surfaces of shoulders 861 from damaged during the cutting or dicing process, and allowing them to be used as alignment references. Similarly, a bottom half collimator can be molded with recollimating elements such that when a similar notch is cut or diced the shoulder is protected from damage during dicing or cutting and may be used as an alignment reference.

FIG. 8F depicts a view of a half collimator array with a notch 863 molded between the focusing elements 820B on the bottom surface of a solid substrate such that when cut or diced, a removed volume 867 will not remove material past shoulders 861, allowing both surfaces of shoulders 861 to be utilized for registering the position of the half collimator array—i.e., references for alignment. Similarly, a bottom half collimator can be molded between recollimating elements on the bottom surface of a solid substrate such that when cut or diced a removed volume will not remove material past shoulders, allowing both surfaces of shoulders to be utilized for registering position of bottom half collimator—i.e., references for alignment.

In this disclosure, the terms "focusing elements" and "recollimating elements" are used for convenience of explanation. Any optical element having a focal point can be encompassed by these terms. Also, it is apparent that the spatial filters disclosed herein can be used in actual operation not only in the forward direction as described above, but also in a reversed direction. For example, in the example shown in FIGS. 7A-7D, light to be filtered may be configured to enter the spatial filter from the side of the recollimating element 720C and exit from the focusing element 720B. Depending on the particular design of the spatial filter, the light passage direction when forming the pinhole may be opposite to the light passage direction in actual filter usage. In certain applications, this arrangement is preferable because it yields a better spatial filter performance. Furthermore, in this disclosure, the term "spatial filter" is used to encompass broadly any optical elements having a function of rejecting any components of light. For example, a simple slit or hole that blocks part of incident light is encompassed by the term "spatial filter." An angular filter that rejects off-axis light rays is also encompassed by this term. Thus, the term "spatial filter" as used in the title or the preamble of claims of any patents issuing from this disclosure does not limit the scope of the claims in any way, which shall be set forth by elements or steps specifically recited in the respective claims. Further, the term "opaque" as in an opaque layer or material or similar terms as used in this specification includes any layer or material that is substantially non-transparent to light over a design wavelength range, such as a reflective layer or material or an absorbing layer or material or the like.

In some of the embodiments described above, the upper piece (such as slug A and top half collimator 700) is fabricated with a self-aligned pinhole, and a lower piece without a pinhole (such as slug B and bottom half collimator 700A) is attached to the upper piece to construct a spatial filter. Alternatively, both pieces may be made with a self-aligned pinhole by the methods described above, and attached and bonded together such that the pinholes are substantially aligned.

As disclosed above, at least some of the embodiments of the present invention are suited for high volume production of mid-grade spatial filter modules. Also, inexpensive, portable spatial filters that can be incorporated into portable optical analysis devices can be provided. In accordance with at least some of the embodiments disclosed above, pinhole fabrication steps ensure that the pinhole is intrinsically self-aligned to the optical axis so that there is no need to provide for adjustment mechanisms of the type typically found in high-end spatial filter instruments. Thus, as described above, non-adjustable fixed support members, such as the frame 580 of FIG. 5A and the solid substrate 785 and 782 in FIG. 7C as described above, can be used to define the spacing between the two oppositely disposed focusing elements and the middle plate having a pinhole. Thus, once built, the spatial filters of at least some of the embodiments of the present invention have no risk of drifting due to shock or impact and therefore will not require periodic realignment. Performance may still be affected by thermal expansion of materials.

It will be apparent to those skilled in the art that various modifications and variations can be made without departing from the spirit or scope of the invention. Thus, it is intended that the disclosed embodiments cover modifications and variations that come within the scope of the claims that eventually issue in a patent(s) originating from this application and their equivalents. In particular, it is explicitly contemplated that any part or whole of any two or more of the embodiments and their modifications described above can be combined in whole or in part.

What is claimed is:

1. A method for making a spatial filter, comprising:
    forming a structure having a focusing element and an opaque surface, the opaque surface being disposed remotely from the focusing element in substantially the same plane as a focal plane of the focusing element, the opaque surface having no pinhole yet formed therein;
    forming a self-aligned pinhole in the opaque surface at or adjacent to a focal point of the focusing element by transmitting a substantially collimated monochromatic laser light beam through the focusing element so that a point optimally corresponding to the focal point is identified on the opaque surface and any aberration or anomalies due to imperfection of the focusing element, if any, is reflected on the shape and position of the pinhole so formed, thereby making a spatial filter component constituted of the focusing element and the opaque surface with the self-aligned pinhole.

2. The method according to claim 1, wherein the opaque surface is made of a metal layer, and
    wherein the step of forming the self-aligned pinhole includes radiating the laser light beam to the metal layer through the focusing element to ablate a portion of the metal at or adjacent to the focal point, thereby forming the self-aligned pinhole in the metal layer.

3. The method according to claim 1, wherein the step of forming the self-aligned pinhole includes:
    forming a photoresist on the opaque surface;
    radiating an exposing light beam to the photoresist through the focusing element to expose the photoresist; and
    developing the exposed photoresist to form a photoresist pattern that defines a position of the pinhole to be formed.

4. The method according to claim 1, wherein the step of forming said structure includes:
    making a piece of block from a substantially transparent material, said block having a lens face and a planar face, the planar face being disposed in substantially the same plane as a focal plane of the lens face; and
    depositing a metal layer on the planar face.

5. The method according to claim 1, wherein the step of forming said structure includes:
    attaching a focusing element to a block, the block having a planar face in substantially the same plane as a focal plane of the focusing element; and
    attaching an opaque plate on the planar face.

6. The method according to claim 1, further comprising:
    forming a second focusing element optically coupled to said structure, said second focusing element having a focal point substantially coincident with the focal point of said focusing element so that light transmitting through the focusing element, the pinhole, and the second focusing element in this order and in a reversed order is substantially collimated.

7. The method according to claim 6,
    wherein the step of forming said structure includes:
    making two substantially identical pieces of block from a substantially transparent material, each of said blocks having a lens face and a planar face, the planar face being disposed in substantially the same plane as a focal plane of the lens face; and
    depositing a metal layer on the planar face of one of the two substantially identical pieces of block, and
    wherein the step of forming the second focusing element includes bonding the other one of the two substantially identical pieces of block to the said structure having the pinhole formed therein such that the planar face having the metal layer formed thereon of said one of the two blocks is abutted on the planar face of the other block.

8. The method according to claim 1, further comprising:
    forming a second structure having a second focusing element and a second opaque surface, the second opaque surface being disposed remotely from the second focusing element in substantially the same plane as a focal plane of the second focusing element;
    forming a second pinhole in the second opaque surface of the second structure at or adjacent to a focal point of the second focusing element by transmitting a substantially collimated light beam through the second focusing element so that a point optimally corresponding to the focal point is identified on the second opaque surface and imperfection of the second focusing element, if any, is reflected on the shape and position of the second pinhole so formed; and
    thereafter, bonding said structure with the pinhole and said second structure with the second pinhole such that the pinhole of said structure and the second pinhole of said second structure are substantially aligned to each other.

* * * * *